(12) United States Patent
Belson et al.

(10) Patent No.: US 11,998,804 B2
(45) Date of Patent: Jun. 4, 2024

(54) REPETITION PHASE DETECTION

(71) Applicant: Tonal Systems, Inc., San Francisco, CA (US)

(72) Inventors: Brandt Belson, San Francisco, CA (US); Egor Ponomarev, Samara (RU)

(73) Assignee: Tonal Systems, Inc., San Francisco, CA (US)

( * ) Notice: Subject to any disclaimer, the term of this patent is extended or adjusted under 35 U.S.C. 154(b) by 160 days.

(21) Appl. No.: 17/242,097

(22) Filed: Apr. 27, 2021

(65) Prior Publication Data

US 2022/0339498 A1   Oct. 27, 2022

(51) Int. Cl.
A63B 24/00   (2006.01)

(52) U.S. Cl.
CPC ...... *A63B 24/0062* (2013.01); *A63B 24/0087* (2013.01); *A63B 2024/0093* (2013.01); *A63B 2220/803* (2013.01)

(58) Field of Classification Search
CPC ............ A63B 24/0062; A63B 24/0087; A63B 2024/0093; A63B 2220/803
See application file for complete search history.

(56) References Cited

U.S. PATENT DOCUMENTS

| | | |
|---|---|---|
| 3,465,592 A | 9/1969 | Perrine |
| 3,511,225 A | 5/1970 | Gunpei |
| 3,953,025 A | 4/1976 | Mazman |
| 4,261,562 A | 4/1981 | Flavell |
| 4,616,823 A | 10/1986 | Yang |
| 4,798,378 A | 1/1989 | Jones |
| 4,817,939 A | 4/1989 | Augspurger |
| 4,869,497 A | 9/1989 | Stewart |
| 4,898,381 A | 2/1990 | Gordon |
| 5,020,794 A | 6/1991 | Englehardt |
| 5,042,798 A | 8/1991 | Sawicky |
| 5,104,121 A | 4/1992 | Webb |
| 5,117,170 A | 5/1992 | Keane |
| 5,265,589 A | 11/1993 | Wang |
| 5,277,684 A | 1/1994 | Harris |
| 5,360,382 A | 11/1994 | Chi |

(Continued)

FOREIGN PATENT DOCUMENTS

| | | |
|---|---|---|
| CN | 2681776 | 3/2005 |
| CN | 2683184 | 3/2005 |

(Continued)

OTHER PUBLICATIONS

Espacenet, Machine translation of KR20140124161 Description (Year: 2014).

(Continued)

*Primary Examiner* — Sundhara M Ganesan
*Assistant Examiner* — Jacqueline N L Loberiza
(74) *Attorney, Agent, or Firm* — Van Pelt, Yi & James LLP

(57) ABSTRACT

Controlling an exercise machine includes receiving a stream of measurements of extension of a component of an exercise machine. It further includes detecting a first phase of a repeated motion. It further includes detecting a transition to a second phase of the repeated motion. A time constraint is applied to the detection of the transition to the second phase of the repeated motion. It further includes controlling a resistance associated with the second phase of the repeated motion.

21 Claims, 9 Drawing Sheets

(56) References Cited

U.S. PATENT DOCUMENTS

| | | | |
|---|---|---|---|
| 5,433,678 A | 7/1995 | Chi | |
| 5,569,121 A | 10/1996 | Sellier | |
| 5,583,403 A | 12/1996 | Anjanappa | |
| 5,588,938 A | 12/1996 | Schneider | |
| 5,624,353 A | 4/1997 | Naidus | |
| 5,697,869 A | 12/1997 | Ehrenfried | |
| 5,830,116 A | 11/1998 | Gautier | |
| 5,897,444 A | 4/1999 | Hellyer | |
| 5,993,356 A | 11/1999 | Houston | |
| 6,027,429 A | 2/2000 | Daniels | |
| 6,142,919 A | 11/2000 | Jorgensen | |
| 6,227,047 B1 | 5/2001 | Livingston | |
| 6,238,323 B1 | 5/2001 | Simonson | |
| 6,280,361 B1 | 8/2001 | Harvey | |
| 6,443,877 B1 | 9/2002 | Hoecht | |
| 6,508,748 B1 | 1/2003 | Ish, III | |
| 6,547,702 B1 | 4/2003 | Heidecke | |
| 7,682,287 B1 | 3/2010 | Hsieh | |
| 7,686,746 B2 | 3/2010 | Koyama | |
| 7,695,418 B2 | 4/2010 | Ish, III | |
| 7,885,785 B1 | 2/2011 | Pekarek | |
| 7,909,742 B2 | 3/2011 | Ish, III | |
| 7,985,166 B2 | 7/2011 | Farnsworth | |
| 7,998,033 B1 | 8/2011 | Schroeder | |
| 7,998,036 B2 | 8/2011 | Ish, III | |
| 8,057,367 B2 | 11/2011 | Giannelli | |
| 8,096,926 B1 | 1/2012 | Batca | |
| 8,287,434 B2 | 10/2012 | Zavadsky | |
| 8,308,620 B2 | 11/2012 | Grzegorz | |
| 8,333,681 B2 | 12/2012 | Schmidt | |
| 8,337,364 B2 | 12/2012 | Ishii | |
| 8,388,499 B1 | 3/2013 | Rindfleisch | |
| 8,475,338 B2 | 7/2013 | Greenhill | |
| 8,517,899 B2 | 8/2013 | Zhou | |
| 8,727,946 B2 | 5/2014 | Greenhill | |
| 8,834,328 B1 | 9/2014 | Batca | |
| 8,845,499 B1 | 9/2014 | Boatwright | |
| 8,900,097 B1 | 12/2014 | Griggs | |
| 8,900,099 B1 | 12/2014 | Boyette | |
| 8,968,155 B2 | 3/2015 | Bird | |
| 9,211,434 B2 | 12/2015 | Giannelli | |
| 9,457,220 B2 | 10/2016 | Olson | |
| 9,656,116 B2 | 5/2017 | Giannelli | |
| 9,700,753 B1 | 7/2017 | Boatwright | |
| 9,861,856 B1 | 1/2018 | Miller | |
| 9,901,766 B2 | 2/2018 | Ross | |
| 9,901,768 B1 | 2/2018 | Wu | |
| 9,999,795 B1 | 6/2018 | Jarosz | |
| 10,004,945 B2 | 6/2018 | Sauter | |
| 10,143,880 B1 | 12/2018 | Boatwright | |
| 10,220,235 B2 | 3/2019 | Norris | |
| 10,258,821 B2 | 4/2019 | Jeong | |
| 10,265,572 B2 | 4/2019 | Bach | |
| 10,286,253 B1 | 5/2019 | Johnson | |
| 10,335,626 B2 | 7/2019 | Orady | |
| 10,441,840 B2 | 10/2019 | Dalebout | |
| 10,486,015 B2 | 11/2019 | Valente | |
| 10,500,442 B2 | 12/2019 | Hong | |
| 10,549,152 B2 | 2/2020 | Walker | |
| 10,589,163 B2 | 3/2020 | Orady | |
| 10,596,056 B2 | 3/2020 | Hou | |
| 10,709,925 B2 | 7/2020 | Dalebout | |
| 10,758,767 B2 | 9/2020 | Olson | |
| 11,040,231 B2 | 6/2021 | Rubin | |
| 11,097,148 B2 | 8/2021 | Kennington | |
| 11,110,317 B2 | 9/2021 | Valente | |
| 11,123,592 B2 | 9/2021 | Orady | |
| 2001/0023221 A1 | 9/2001 | Simonson | |
| 2003/0017918 A1 | 1/2003 | Webb | |
| 2003/0032535 A1 | 2/2003 | Wang | |
| 2003/0134722 A1 | 7/2003 | Greenland | |
| 2003/0153438 A1 | 8/2003 | Gordon | |
| 2003/0171192 A1 | 9/2003 | Wu | |
| 2003/0176261 A1 | 9/2003 | Simonson | |
| 2003/0207734 A1 | 11/2003 | LaStayo | |
| 2004/0009848 A1 | 1/2004 | Lee | |
| 2004/0082438 A1 | 4/2004 | LaStayo | |
| 2004/0092369 A1 | 5/2004 | Slawinski | |
| 2004/0157711 A1 | 8/2004 | Regev | |
| 2005/0143226 A1 | 6/2005 | Heidecke | |
| 2005/0143230 A1 | 6/2005 | Dalebout | |
| 2006/0006836 A1 | 1/2006 | Miehlich | |
| 2006/0040799 A1 | 2/2006 | Pompile | |
| 2006/0069336 A1 | 3/2006 | Krebs | |
| 2006/0229164 A1 | 10/2006 | Einav | |
| 2006/0234840 A1 | 10/2006 | Watson | |
| 2007/0015096 A1 | 1/2007 | Soller | |
| 2007/0054785 A1 | 3/2007 | Drechsler | |
| 2007/0117691 A1 | 5/2007 | Sechrest | |
| 2007/0129223 A1 | 6/2007 | Kolomeir | |
| 2007/0142187 A1 | 6/2007 | Kolomeir | |
| 2007/0155587 A1 | 7/2007 | Huang | |
| 2007/0161470 A1 | 7/2007 | Berryman | |
| 2007/0161472 A1 | 7/2007 | Drechsler | |
| 2007/0173384 A1 | 7/2007 | Sechrest | |
| 2007/0202992 A1 | 8/2007 | Grasshoff | |
| 2007/0259759 A1 | 11/2007 | Sumners | |
| 2008/0051263 A1 | 2/2008 | Rasmussen | |
| 2008/0051267 A1 | 2/2008 | Ish, III | |
| 2008/0161733 A1 | 7/2008 | Einav | |
| 2008/0248926 A1* | 10/2008 | Cole | A63B 21/0628 482/5 |
| 2008/0294074 A1 | 11/2008 | Tong | |
| 2008/0300116 A1 | 12/2008 | Eder | |
| 2009/0023561 A1 | 1/2009 | Ross | |
| 2009/0029835 A1 | 1/2009 | Ellis | |
| 2009/0036277 A1 | 2/2009 | Ish, III | |
| 2009/0075791 A1 | 3/2009 | Kissel | |
| 2009/0111666 A1 | 4/2009 | Wang | |
| 2009/0114892 A1 | 5/2009 | Lesko | |
| 2009/0170675 A1 | 7/2009 | Giannelli | |
| 2009/0221403 A1 | 9/2009 | Chan | |
| 2010/0001177 A1 | 1/2010 | Dolenti | |
| 2010/0069202 A1 | 3/2010 | Olsen | |
| 2010/0144496 A1 | 6/2010 | Schmidt | |
| 2010/0144497 A1 | 6/2010 | Clark | |
| 2010/0298097 A1 | 11/2010 | Preumont | |
| 2010/0311552 A1 | 12/2010 | Sumners | |
| 2010/0331148 A1 | 12/2010 | Huang | |
| 2011/0152045 A1 | 6/2011 | Horne | |
| 2011/0172058 A1 | 7/2011 | Deaconu | |
| 2011/0183816 A1 | 7/2011 | Giannelli | |
| 2011/0275481 A1 | 11/2011 | Greenhill | |
| 2011/0294630 A1 | 12/2011 | Reyes | |
| 2012/0021876 A1 | 1/2012 | Hsiung | |
| 2012/0053014 A1 | 3/2012 | Zhu | |
| 2012/0088634 A1 | 4/2012 | Heidecke | |
| 2012/0231929 A1 | 9/2012 | Hsieh | |
| 2012/0279801 A1 | 11/2012 | Watson | |
| 2013/0095978 A1 | 4/2013 | Sauter | |
| 2013/0157816 A1 | 6/2013 | Lyszczarz | |
| 2013/0172153 A1 | 7/2013 | Watterson | |
| 2013/0289452 A1 | 10/2013 | Smith | |
| 2013/0296144 A1 | 11/2013 | Gvoich | |
| 2013/0331239 A1 | 12/2013 | Richards | |
| 2014/0038777 A1 | 2/2014 | Bird | |
| 2014/0113779 A1 | 4/2014 | Loach | |
| 2014/0121071 A1 | 5/2014 | Strom | |
| 2014/0194250 A1 | 7/2014 | Reich | |
| 2014/0194251 A1 | 7/2014 | Reich | |
| 2014/0226963 A1 | 8/2014 | Ryan | |
| 2014/0228175 A1 | 8/2014 | Lemos | |
| 2015/0020620 A1 | 1/2015 | Garner | |
| 2015/0133828 A1 | 5/2015 | Hachisuka | |
| 2015/0148194 A1 | 5/2015 | Bird | |
| 2015/0165272 A1 | 6/2015 | Bird | |
| 2015/0190667 A1 | 7/2015 | Balandis | |
| 2015/0258381 A1 | 9/2015 | Suzuki | |
| 2015/0297934 A1 | 10/2015 | Agrawal | |
| 2015/0335950 A1 | 11/2015 | Eder | |
| 2015/0367162 A1 | 12/2015 | Mueller | |
| 2016/0101322 A1 | 4/2016 | Potter | |
| 2016/0158603 A1 | 6/2016 | Darwood | |
| 2016/0193497 A1 | 7/2016 | Arst | |

(56) References Cited

U.S. PATENT DOCUMENTS

| | | |
|---|---|---|
| 2016/0243402 A1 | 8/2016 | Finadri |
| 2016/0249832 A1 | 9/2016 | Carter |
| 2016/0332019 A1 | 11/2016 | Rollins |
| 2016/0332020 A1 | 11/2016 | Chen |
| 2016/0346617 A1 | 12/2016 | Srugo |
| 2016/0354638 A1 | 12/2016 | Carr |
| 2017/0095695 A1* | 4/2017 | Mangusson ........ A63B 21/4047 |
| 2017/0173396 A1 | 6/2017 | Lu |
| 2017/0197103 A1 | 7/2017 | Rau |
| 2017/0239124 A1 | 8/2017 | Cunningham |
| 2017/0239517 A1 | 8/2017 | Jeong |
| 2017/0246507 A1 | 8/2017 | Kennington |
| 2017/0266481 A1 | 9/2017 | Dalebout |
| 2017/0282015 A1 | 10/2017 | Wicks |
| 2017/0319905 A1 | 11/2017 | O'Connor |
| 2017/0333756 A1 | 11/2017 | Bird |
| 2017/0361165 A1 | 12/2017 | Miller |
| 2018/0001181 A1 | 1/2018 | Von Prellwitz |
| 2018/0021614 A1 | 1/2018 | Taft |
| 2018/0021616 A1 | 1/2018 | Orady |
| 2018/0160943 A1 | 6/2018 | Fyfe |
| 2018/0214729 A1 | 8/2018 | Rubin |
| 2018/0214730 A1 | 8/2018 | Larose |
| 2018/0290001 A1 | 10/2018 | Baek |
| 2018/0326243 A1 | 11/2018 | Badi |
| 2018/0361200 A1 | 12/2018 | Walker |
| 2019/0001183 A1 | 1/2019 | Liao |
| 2019/0046830 A1 | 2/2019 | Chiavegato |
| 2019/0099632 A1 | 4/2019 | Orady |
| 2019/0099633 A1 | 4/2019 | Orady |
| 2019/0099637 A1 | 4/2019 | Valente |
| 2019/0099652 A1 | 4/2019 | Orady |
| 2019/0126099 A1 | 5/2019 | Hoang |
| 2019/0160324 A1 | 5/2019 | Leopoldo Da Camara Filho |
| 2020/0047027 A1 | 2/2020 | Ward |
| 2020/0047030 A1 | 2/2020 | Ward |
| 2020/0047053 A1 | 2/2020 | Ward |
| 2020/0047054 A1 | 2/2020 | Ward |
| 2020/0047055 A1 | 2/2020 | Ward |
| 2020/0054929 A1 | 2/2020 | Ward |
| 2021/0008402 A1 | 1/2021 | Orady |
| 2021/0379436 A1 | 12/2021 | Orady |
| 2022/0032114 A1 | 2/2022 | Valente |

FOREIGN PATENT DOCUMENTS

| | | |
|---|---|---|
| CN | 2817911 | 9/2006 |
| CN | 201631963 | 11/2010 |
| CN | 202554808 | 11/2012 |
| CN | 102671346 | 4/2014 |
| CN | 204219688 | 3/2015 |
| CN | 105498151 | 4/2016 |
| CN | 206508201 | 9/2017 |
| DE | 202006006751 | 6/2006 |
| EP | 3202465 | 8/2017 |
| FR | 2968571 | 1/2013 |
| JP | 62179478 | 8/1987 |
| JP | 07227439 | 8/1995 |
| JP | H10203467 | 8/1998 |
| JP | 11342226 | 12/1999 |
| JP | 3096472 | 9/2003 |
| JP | 2006187317 | 7/2006 |
| JP | 2015031511 | 2/2015 |
| KR | 100847515 | 7/2008 |
| KR | 101160960 | 6/2012 |
| KR | 101166981 | 7/2012 |
| KR | 20140124161 | 10/2014 |
| TW | 397837 | 2/2011 |
| WO | 1988001185 | 2/1988 |
| WO | 1991012854 | 9/1991 |
| WO | 2009061178 | 5/2009 |
| WO | 2009143808 | 12/2009 |
| WO | 2016171799 | 10/2016 |
| WO | 2018022465 | 2/2018 |

OTHER PUBLICATIONS

Brakel, J.P.G. Van. "Robust peak detection algorithm using z-scores". Stack Overflow. 2014 (version: Nov. 8, 2020).

* cited by examiner

REPETITION PHASE DETECTION

BACKGROUND OF THE INVENTION

Repetitions form one component of exercise routines, where various actions and performance measures may be determined relative to repetitions. However, due to variation in the way that users move when performing exercises, it can be difficult to monitor repetitions.

BRIEF DESCRIPTION OF THE DRAWINGS

Various embodiments of the invention are disclosed in the following detailed description and the accompanying drawings.

DETAILED DESCRIPTION

Figure 1A:
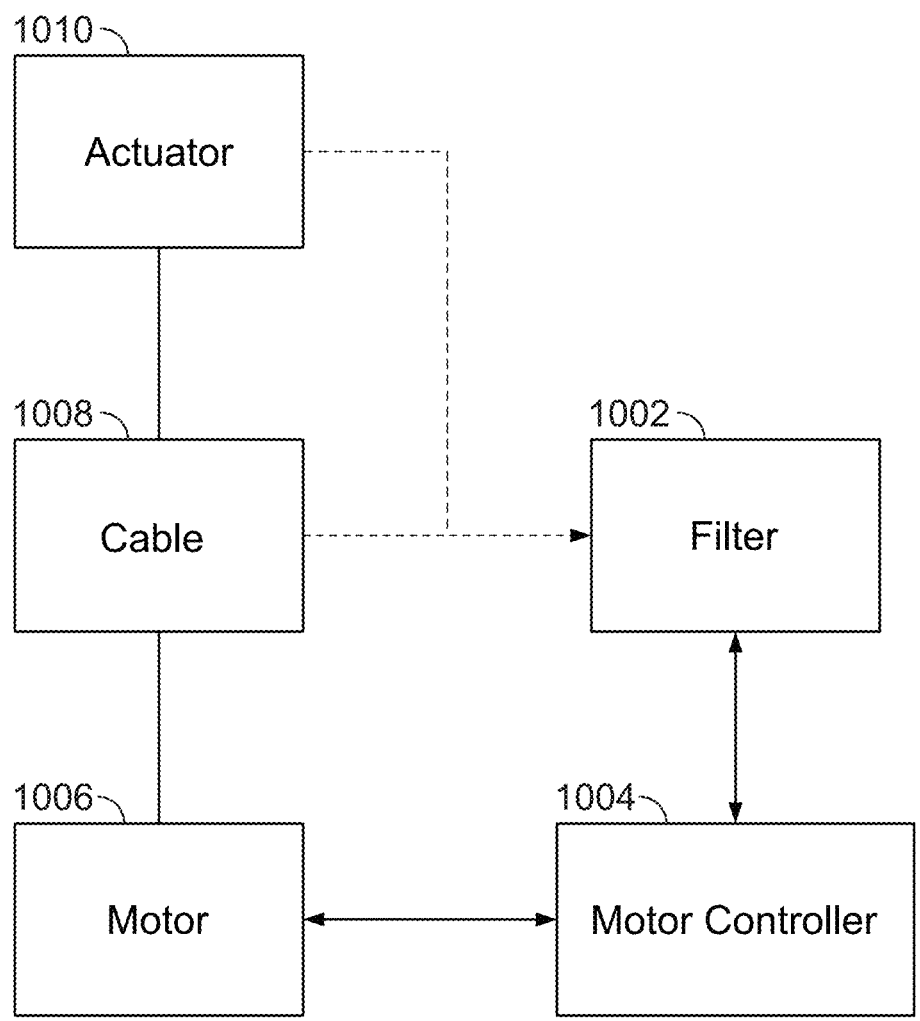
FIG. 1A illustrates an embodiment of an exercise machine.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Described herein are techniques for detecting a first repetition of an exercise in a set. Techniques for detecting phases of a repetition are also described herein. The techniques for first repetition detection and detection of phases of a repetition described herein may be used to control an exercise machine.

In some embodiments, controlling an exercise machine based on detection of a first repetition includes receiving a stream of measurements of extension of a component of the exercise machine. The stream of measurements is characterized, including detecting at least one extremum having at least one extremum parameter. The extremum parameter is matched with a previously determined signature associated with a user. An output of the exercise machine is changed based on the match.

In some embodiments, controlling an exercise machine based on detection of phases of a repetition includes receiving a stream of measurements of extension of a component of the exercise machine. A first phase of a repeated motion is detected. A transition to a second phase of the repeated motion is detected. A time constraint is applied to the detection of the transition to the second phase of the repeated motion. A resistance associated with the second phase of the repeated motion is controlled.

For illustrative purposes, embodiments of controlling a digital strength training exercise machine based on detection of a first repetition and detection of phases of a repetition are described. The techniques for controlling an exercise machine described herein may be variously adapted to accommodate any other type of exercise machine, such as other cable resistance exercise machines, as appropriate.

Example Digital Strength Trainer

FIG. 1A illustrates an embodiment of an exercise machine. In particular, the exercise machine of FIG. 1A is an example of a digital strength training machine. In some embodiments, a digital strength trainer uses electricity to generate tension/resistance. Examples of electronic resistance include using an electromagnetic field to generate tension/resistance, using an electronic motor to generate tension/resistance, and using a three-phase brushless direct-current (BLDC) motor to generate tension/resistance. In various embodiments, the form detection and feedback techniques described herein may be variously adapted to accommodate other types of exercise machines using different types of load elements without limitation, such as exercise machines based on pneumatic cylinders, springs, weights, flexing nylon rods, elastics, pneumatics, hydraulics, and/or friction.

Such a digital strength trainer using electricity to generate tension/resistance is also versatile by way of using dynamic resistance, such that tension/resistance may be changed nearly instantaneously. When tension is coupled to position of a user against their range of motion, the digital strength trainer may apply arbitrary applied tension curves, both in terms of position and in terms of phase of the movement: concentric, eccentric, and/or isometric. Furthermore, the shape of these curves may be changed continuously and/or in response to events; the tension may be controlled continuously as a function of a number of internal and external variables including position and phase, and the resulting applied tension curve may be pre-determined and/or adjusted continuously in real time.

The example exercise machine of FIG. 1A includes the following:
- a motor controller circuit (1004), which in some embodiments includes a processor, inverter, pulse-width-modulator, and/or a Variable Frequency Drive (VFD);
- a motor (1006), for example, a three-phase brushless DC driven by the controller circuit (1004). While a single motor is shown in this example, other numbers of motors may be used. For example, dual motors may be used;
- a spool/hub with a cable (1008) wrapped around the spool and coupled to the spool. On the other end of the cable an actuator (1010) is coupled in order for a user to grip and pull on. Examples of actuators include handles and bars that are attached to the cables. The actuators may be attached to the cables at distal ends of the arms of the exercise machine, which are described in further detail below. The spool is coupled to the motor (1006) either directly or via a shaft/belt/chain/gear mechanism;
- a filter (1002), to digitally control the controller circuit (1004) based on receiving information from the cable (1008) and/or actuator (1010);
- optionally (not shown in FIG. 1A) a gearbox between the motor and spool. Gearboxes multiply torque and/or friction, divide speed, and/or split power to multiple spools. A number of combinations of motor and gearbox may also be used. A cable-pulley system may be used in place of a gearbox, and/or a dual motor may be used in place of a gearbox;
- one or more of the following sensors (not shown in FIG. 1A):
- encoders: In various embodiments, encoders are used to measure cable lengths (e.g., left and right cable lengths in this example), cable speeds, weight (tension), etc.

One example of an encoder is a position encoder; a sensor to measure position of the actuator (1010) or motor (1006). Examples of position encoders include a hall effect shaft encoder, grey-code encoder on the motor/spool/cable (1008), an accelerometer in the actuator/handle (1010), optical sensors, position measurement sensors/methods built directly into the motor (1006), and/or optical encoders. In one embodiment, an optical encoder is used with an encoding pattern that uses phase to determine direction associated with the low resolution encoder. Other mechanisms that measure back-EMF (back electromagnetic force) from the motor (1006) in order to calculate position may also be used;
- a motor power sensor; a sensor to measure voltage and/or current being consumed by the motor (1006);
- a user tension sensor; a torque/tension/strain sensor and/or gauge to measure how much tension/force is being applied to the actuator (1010) by the user. In one embodiment, a tension sensor is built into the cable (1008). Alternatively, a strain gauge is built into the motor mount holding the motor (1006). As the user pulls on the actuator (1010), this translates into strain on the motor mount which is measured using a strain gauge in a Wheatstone bridge configuration. In another embodiment, the cable (1008) is guided through a pulley coupled to a load cell. In another embodiment, a belt coupling the motor (1006) and cable spool or gearbox (1008) is guided through a pulley coupled to a load cell. In another embodiment, the resistance generated by the motor (1006) is characterized based on the voltage, current, or frequency input to the motor.

Another example of sensors includes inertial measurement units (IMUs). In some embodiments, IMUs are used to measure the acceleration and rate of rotation of actuators. The IMUs may be embedded within or attached to actuators (e.g., in both handles or as an attachment on a bar).

In some embodiments, an IMU is placed on the cable (e.g., via a clip) to determine inertial measurements with respect to the cable. As another example, IMUs may be included in a device that clips onto an actuator accessory such as a bar handle.

Another example type of sensor used by the exercise machine includes cameras.

In some embodiments, the exercise machine includes an embedded camera.

In some embodiments, the exercise machine is communicatively coupled (either in a wired or wireless manner) with a dedicated accessory camera external to the exercise machine that is paired with the exercise machine. The dedicated accessory camera may be set up in a different location to the exercise machine, such as on an adjacent wall, above the exercise machine on the same wall, on a tripod, etc.

In some embodiments, the exercise machine is paired with an external device that has or is attached to a camera, where such devices include mobile phones, tablets, computers, etc.

Various types of cameras may be used. As one example, RGB cameras are used. As another example, cameras with depth-sensing capability are used.

In some embodiments, infrared cameras are used that measure heat, where in some embodiments such information is used to deduce quantities such as muscle exertion, soreness, etc.

In some embodiments, the sensors used by the exercise machine include accessories such as smart watches, with which the exercise machine may be communicatively coupled (e.g., via a wireless connection such as Bluetooth or WiFi). The readings from such sensors may then be used to monitor form.

Other examples of accessories that may be communicatively coupled with the exercise machine include: smart clothing that measures muscle engagement or movement; and smart mats or smart benches that measure spatial distribution of force when the user is on them.

In some embodiments, the exercise machine includes mechanisms to locate devices (e.g., actuators, IMUs, etc.) in 3-Dimensional space. As one example, Bluetooth Low Energy (BLE) spatial locationing (e.g., Angle of Arrival and Angle of Departure "AoA/AoD") is used to locate devices in 3-D space.

In one embodiment, a three-phase brushless DC motor (1006) is used with the following:
- a controller circuit (1004) combined with the filter (1002) that includes:
  - a processor that runs software instructions;
  - three pulse width modulators (PWMs), each with two channels, modulated at 20 kHz;
  - six transistors in an H-Bridge configuration coupled to the three PWMs;
  - optionally, two or three ADCs (Analog to Digital Converters) monitoring current on the H-Bridge; and/or
  - optionally, two or three ADCs monitoring back-EMF voltage;
- the three-phase brushless DC motor (1006), which in some embodiments includes a synchronous-type and/or asynchronous-type permanent magnet motor, such that:
  - the motor (1006) may be in an "out-runner configuration" as described below;

the motor (1006) may have a maximum torque output of at least 60 Nm and a maximum speed of at least 300 RPMs;

optionally, with an encoder or other method to measure motor position;

a cable (1008) wrapped around the body of the motor (1006) such that the entire motor (1006) rotates, so the body of the motor is being used as a cable spool in one embodiment. Thus, the motor (1006) is directly coupled to a cable (1008) spool. In one embodiment, the motor (1006) is coupled to a cable spool via a shaft, gearbox, belt, and/or chain, allowing the diameter of the motor (1006) and the diameter of the spool to be independent, as well as introducing a stage to add a set-up or step-down ratio if desired. Alternatively, the motor (1006) is coupled to two spools with an apparatus in between to split or share the power between those two spools. Such an apparatus could include a differential gearbox, or a pulley configuration; In some embodiments, the two motors (dual motor configuration) are each coupled with a respective spool.

an actuator (1010) such as a handle, a bar, a strap, or other accessory connected directly, indirectly, or via a connector such as a carabiner to the cable (1008).

In some embodiments, the controller circuit (1002, 1004) is programmed to drive the motor in a direction such that it draws the cable (1008) towards the motor (1006). The user pulls on the actuator (1010) coupled to the cable (1008) against the direction of pull of the motor (1006).

One example purpose of this setup is to provide an experience to a user similar to using a traditional cable-based strength training machine, where the cable is attached to a weight stack being acted on by gravity. Rather than the user resisting the pull of gravity, they are instead resisting the pull of the motor (1006).

Note that with a traditional cable-based strength training machine, a weight stack may be moving in two directions: away from the ground or towards the ground. When a user pulls with sufficient tension, the weight stack rises, and as that user reduces tension, gravity overpowers the user and the weight stack returns to the ground.

By contrast in a digital strength trainer, there is no actual weight stack. The notion of the weight stack is one modeled by the system. The physical embodiment is an actuator (1010) coupled to a cable (1008) coupled to a motor (1006). A "weight moving" is instead translated into a motor rotating. As the circumference of the spool is known and how fast it is rotating is known, the linear motion of the cable may be calculated to provide an equivalency to the linear motion of a weight stack. Each rotation of the spool equals a linear motion of one circumference or $2\pi r$ for radius r. Likewise, torque of the motor (1006) may be converted into linear force by multiplying it by radius r.

If the virtual/perceived "weight stack" is moving away from the ground, motor (1006) rotates in one direction. If the "weight stack" is moving towards the ground, motor (1006) rotates in the opposite direction. Note that the motor (1006) is pulling towards the cable (1008) onto the spool. If the cable (1008) is unspooling, it is because a user has overpowered the motor (1006). Thus, note a distinction between the direction the motor (1006) is pulling, and the direction the motor (1006) is actually turning.

If the controller circuit (1002, 1004) is set to drive the motor (1006) with, for example, a constant torque in the direction that spools the cable, corresponding to the same direction as a weight stack being pulled towards the ground, then this translates to a specific force/tension on the cable (1008) and actuator (1010). Referring to this force as "Target Tension," in one embodiment, this force is calculated as a function of torque multiplied by the radius of the spool that the cable (1008) is wrapped around, accounting for any additional stages such as gear boxes or belts that may affect the relationship between cable tension and torque. If a user pulls on the actuator (1010) with more force than the Target Tension, then that user overcomes the motor (1006) and the cable (1008) unspools moving towards that user, being the virtual equivalent of the weight stack rising. However, if that user applies less tension than the Target Tension, then the motor (1006) overcomes the user and the cable (1008) spools onto and moves towards the motor (1006), being the virtual equivalent of the weight stack returning.

BLDC Motor. While many motors exist that run in thousands of revolutions per second, an application such as fitness equipment designed for strength training has different requirements and is by comparison a low speed, high torque type application suitable for certain kinds of BLDC motors configured for lower speed and higher torque.

In one embodiment, a specification of such a motor (1006) is that a cable (1008) wrapped around a spool of a given diameter, directly coupled to a motor (1006), behaves like a 200 lbs weight stack, with the user pulling the cable at a maximum linear speed of 62 inches per second. The aforementioned weight and linear speed specifications are but examples for illustrative purposes, and the system may be configured to behave to different specifications. A number of motor parameters may be calculated based on the diameter of the spool.

TABLE 1

| | User Requirements | | | | | |
|---|---|---|---|---|---|---|
| Target Weight | 200 lbs | | | | | |
| Target Speed | 62 inches/sec = 1.5748 meters/sec | | | | | |

| | Requirements by Spool Size | | | | | |
|---|---|---|---|---|---|---|
| Diameter (inches) | 3 | 5 | 6 | 7 | 8 | 9 |
| RPM | 394.7159 | 236.82954 | 197.35795 | 169.1639572 | 148.0184625 | 131.5719667 |
| Torque (Nm) | 67.79 | 112.9833333 | 135.58 | 158.1766667 | 180.7733333 | 203.37 |
| Circumference (inches) | 9.4245 | 15.7075 | 18.849 | 21.9905 | 25.132 | 28.2735 |

Thus, a motor with 67.79 Nm of force and a top speed of 395 RPM, coupled to a spool with a 3 inch diameter meets these requirements.

Hub motors are three-phase permanent magnet BLDC direct drive motors in an "out-runner" configuration: throughout this specification, the "out-runner" configuration refers to the permanent magnets being placed outside the stator rather than inside, as opposed to many motors which have a permanent magnet rotor placed on the inside of the stator as they are designed more for speed than for torque. Out-runners have the magnets on the outside, allowing for a larger magnet and pole count and are designed for torque over speed. Another way to describe an out-runner configuration is when the shaft is fixed and the body of the motor rotates.

Hub motors also tend to be "pancake style." As described herein, pancake motors are higher in diameter and lower in depth than most motors. Pancake style motors are advantageous for a wall mount, subfloor mount, and/or floor mount application where maintaining a low depth is desirable, such as a piece of fitness equipment to be mounted in a consumer's home or in an exercise facility/area. As described herein, a pancake motor is a motor that has a diameter higher than twice its depth. As one example, a pancake motor is between 15 and 60 centimeters in diameter, for example, 22 centimeters in diameter, with a depth between 6 and 15 centimeters, for example, a depth of 6.7 centimeters.

Motors may also be "direct drive," meaning that the motor does not incorporate or require a gear box stage. Many motors are inherently high speed low torque but incorporate an internal gearbox to gear down the motor to a lower speed with higher torque and may be called gear motors. Direct drive motors may be explicitly called as such to indicate that they are not gear motors.

If a motor does not exactly meet the requirements illustrated in the table above, the ratio between speed and torque may be adjusted by using gears or belts to adjust. A motor coupled to a 9" sprocket, coupled via a belt to a spool coupled to a 4.5" sprocket doubles the speed and halves the torque of the motor. Alternately, a 2:1 gear ratio may be used to accomplish the same thing. Likewise, the diameter of the spool may be adjusted to accomplish the same.

Alternately, a motor with 100× the speed and 100th the torque may also be used with a 100:1 gearbox. As such a gearbox also multiplies the friction and/or motor inertia by 100×, torque control schemes become challenging to design for fitness equipment/strength training applications. Friction may then dominate what a user experiences. In other applications friction may be present, but is low enough that it is compensated for, but when it becomes dominant, it is difficult to control for. For these reasons, direct control of motor torque is more appropriate for fitness equipment/strength training systems. This would typically lead to the selection of an induction type motor for which direct control of torque is simple. Although BLDC motors are more directly able to control speed and/or motor position rather than torque, torque control of BLDC motors can be made possible when used in combination with an appropriate encoder.

Figure 1B:
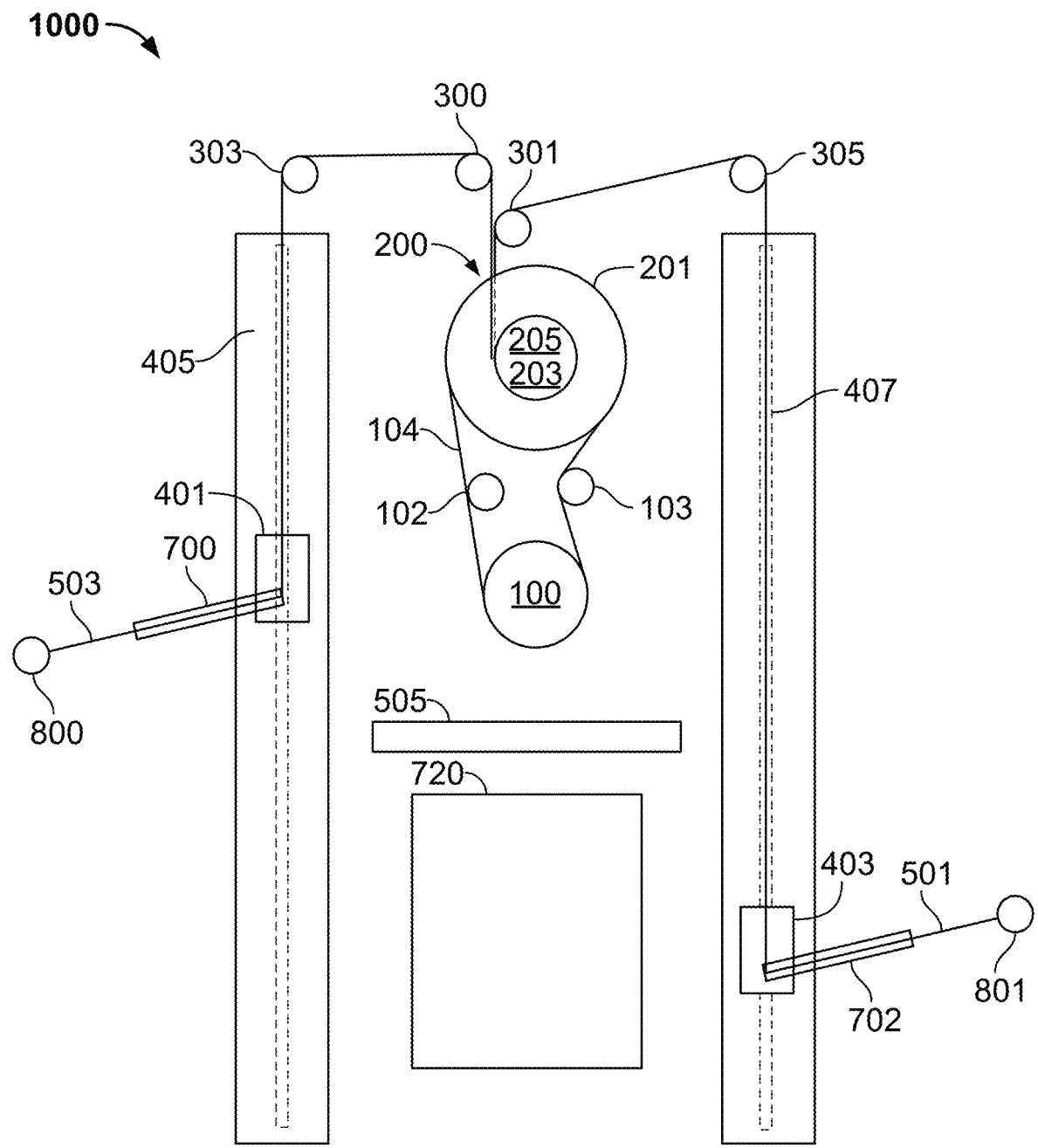
FIG. 1B illustrates a front view of one embodiment of an exercise machine.

FIG. 1B illustrates a front view of one embodiment of an exercise machine. In some embodiments, exercise machine 1000 of FIG. 1B is an example or alternate view of the exercise machine of FIG. 1A. In this example, exercise machine (1000) includes a pancake motor (100), a torque controller coupled to the pancake motor, and a high resolution encoder coupled to the pancake motor (102). As used herein, a "high resolution" encoder refers to an encoder with 30 degrees or greater of electrical angle. In this example, two cables (503) and (501) are coupled respectively to actuators (800) and (801) on one end of the cables. The two cables (503) and (501) are coupled directly or indirectly on the opposite end to the motor (100). While an induction motor may be used for motor (100), a BLDC motor may also be used for its cost, size, weight, and performance. In some embodiments, a high resolution encoder assists the system to determine the position of the BLDC motor to control torque. While an example involving a single motor is shown, the exercise machine may include other configurations of motors, such as dual motors, with each cable coupled to a respective motor.

Sliders (401) and (403) may be respectively used to guide the cable (503) and (501) respectively along rails (405) and (407). The exercise machine in FIG. 1B translates motor torque into cable tension. As a user pulls on actuators (800) and/or (801), the machine creates/maintains tension on cable (503) and/or (501). The actuators (800, 801) and/or cables (503, 501) may be actuated in tandem or independently of one another.

In one embodiment, electronics bay (720) is included and has the necessary electronics to drive the system. In one embodiment, fan tray (505) is included and has fans that cool the electronics bay (720) and/or motor (100).

Motor (100) is coupled by belt (104) to an encoder (102), an optional belt tensioner (103), and a spool assembly (200). In one embodiment, motor (100) is an out-runner, such that the shaft is fixed and the motor body rotates around that shaft. In one embodiment, motor (100) generates torque in the counter-clockwise direction facing the machine, as in the example in FIG. 1B. Motor (100) has teeth compatible with the belt integrated into the body of the motor along the outer circumference. Referencing an orientation viewing the front of the system, the left side of the belt (104) is under tension, while the right side of the belt is slack. The belt tensioner (103) takes up any slack in the belt. An optical rotary encoder (102) coupled to the tensioned side of the belt (104) captures all motor movement, with significant accuracy because of the belt tension. In one embodiment, the optical rotary encoder (102) is a high resolution encoder. In one embodiment, a toothed belt (104) is used to reduce belt slip. The spools rotate counter-clockwise as they are spooling cable/taking cable in, and clockwise as they are unspooling/releasing cable out.

Spool assembly (200) comprises a front spool (203), rear spool (205), and belt sprocket (201). The spool assembly (200) couples the belt (104) to the belt sprocket (201), and couples the two cables (503) and (501) respectively with spools (205) and (203). Each of these components is part of a low profile design. In one embodiment, a dual motor configuration not shown in FIG. 1B is used to drive each cable (503) and (501). In the example shown in FIG. 1B, a single motor (100) is used as a single source of tension, with a plurality of gears configured as a differential are used to allow the two cables/actuators to be operated independently or in tandem. In one embodiment, spools (205) and (203) are directly adjacent to sprocket (201), thereby minimizing the profile of the machine in FIG. 1B.

As shown in FIG. 1B, two arms (700, 702), two cables (503, 501) and two spools (205, 203) are useful for users with two hands, and the principles disclosed without limitation may be extended to three, four, or more arms (700) for quadrupeds and/or group exercise. In one embodiment, the plurality of cables (503, 501) and spools (205, 203) are driven by one sprocket (201), one belt (104), and one motor (100), and so the machine (1000) combines the pairs of devices associated with each user hand into a single device. In other embodiments, each arm is associated with its own motor and spool.

In one embodiment, motor (100) provides constant tension on cables (503) and (501) despite the fact that each of cables (503) and (501) may move at different speeds. For example, some physical exercises may require use of only one cable at a time. For another example, a user may be stronger on one side of their body than another side, causing differential speed of movement between cables (503) and (501). In one embodiment, a device combining dual cables (503) and (501) for a single belt (104) and sprocket (201) retains a low profile, in order to maintain the compact nature of the machine, which can be mounted on a wall.

In one embodiment, pancake style motor(s) (100), sprocket(s) (201), and spools (205, 203) are manufactured and arranged in such a way that they physically fit together within the same space, thereby maximizing functionality while maintaining a low profile.

As shown in FIG. 1B, spools (205) and (203) are respectively coupled to cables (503) and (501) that are wrapped around the spools. The cables (503) and (501) route through the system to actuators (800) and (801), respectively.

The cables (503) and (501) are respectively positioned in part by the use of "arms" (700) and (702). The arms (700) and (702) provide a framework for which pulleys and/or pivot points may be positioned. The base of arm (700) is at arm slider (401) and the base of arm (702) is at arm slider (403).

The cable (503) for a left arm (700) is attached at one end to actuator (800). The cable routes via arm slider (401) where it engages a pulley as it changes direction, then routes along the axis of rotation of track (405). At the top of rail/track (405), fixed to the frame rather than the track, is pulley (303) that orients the cable in the direction of pulley (300), that further orients the cable (503) in the direction of spool (205), wherein the cable (503) is wound around spool (205) and attached to spool (205) at the other end.

Similarly, the cable (501) for a right arm (702) is attached at one end to actuator (801). The cable (501) routes via slider (403) where it engages a pulley as it changes direction, then routes along the axis of rotation of rail/track (407). At the top of the rail/track (407), fixed to the frame rather than the track is pulley (305) that orients the cable in the direction of pulley (301), that further orients the cable in the direction of spool (203), wherein the cable (501) is wound around spool (203) and attached to spool (203) at the other end.

One use of pulleys (300, 301) is that they permit the respective cables (503, 501) to engage respective spools (205, 203) "straight on" rather than at an angle, wherein "straight on" references being within the plane perpendicular to the axis of rotation of the given spool. If the given cable were engaged at an angle, that cable may bunch up on one side of the given spool rather than being distributed evenly along the given spool.

In the example shown in FIG. 1B, pulley (301) is lower than pulley (300). This demonstrates the flexibility of routing cables. In one embodiment, mounting pulley (301) leaves clearance for certain design aesthetic elements that make the machine appear to be thinner.

In one embodiment, the exercise machine/appliance passes a load/resistance against the user via one or more lines/cables, to a grip(s) (examples of an actuator) that a user displaces to exercise. A grip may be positioned relative to the user using a load arm and the load path to the user may be steered using pulleys at the load arm ends, as described above. The load arm may be connected to a frame of the exercise machine using a carriage that moves within a track that may be affixed to the main part of the frame. In one embodiment, the frame is firmly attached to a rigid structure such as a wall. In some embodiments, the frame is not mounted directly to the wall. Instead, a wall bracket is first mounted to the wall, and the frame is attached to the wall bracket. In other embodiments, the exercise machine is mounted to the floor. The exercise machine may be mounted to both the floor and the wall for increased stability. In other embodiments, the exercise machine is a freestanding device.

In some embodiments, the exercise machine includes a media controller and/or processor, which monitors/measures user performance (for example, using the one or more sensors described above), and determines loads to be applied to the user's efforts in the resistance unit (e.g., motor described above). Without limitation, the media controller and processor may be separate control units or combined in a single package. In some embodiments, the controller is further coupled to a display/acoustic channel that allows instructional information to be presented to a user and with which the user interacts in a visual manner, which includes communication based on the eye such as video and/or text or icons, and/or an auditory manner, which includes communication based on the ear such as verbal speech, text-to-speech synthesis, and/or music. Collocated with an information channel is a data channel that passes control program information to the processor which generates, for example, exercise loading schedules. In some embodiments, the display is embedded or incorporated into the exercise machine, but need not be (e.g., the display or screen may be separate from the exercise machine, and may be part of a separate device such as a smartphone, tablet, laptop, etc. that may be communicatively coupled (e.g., either in a wired or wireless manner) to the exercise machine). In one embodiment, the display is a large format, surround screen representing a virtual reality/alternate reality environment to the user; a virtual reality and/or alternate reality presentation may also be made using a headset.

In one embodiment, the appliance media controller provides audio information that is related to the visual information from a program store/repository that may be coupled to external devices or transducers to provide the user with an auditory experience that matches the visual experience. Control instructions that set the operational parameters of the resistance unit for controlling the load or resistance for the user may be embedded with the user information so that the media package includes information usable by the controller to run the machine. In this way a user may choose an exercise regime and may be provided with cues, visual and auditory as appropriate, that allow, for example, the actions of a personal trainer to be emulated. The controller may further emulate the actions of a trainer using an expert system and thus exhibit artificial intelligence. The user may better form a relationship with the emulated coach or trainer, and this relationship may be encouraged by using emotional/mood cues whose effect may be quantified based on performance metrics gleaned from exercise records that track user performance in a feedback loop using, for example, the sensor(s) described above.

Figure 2:
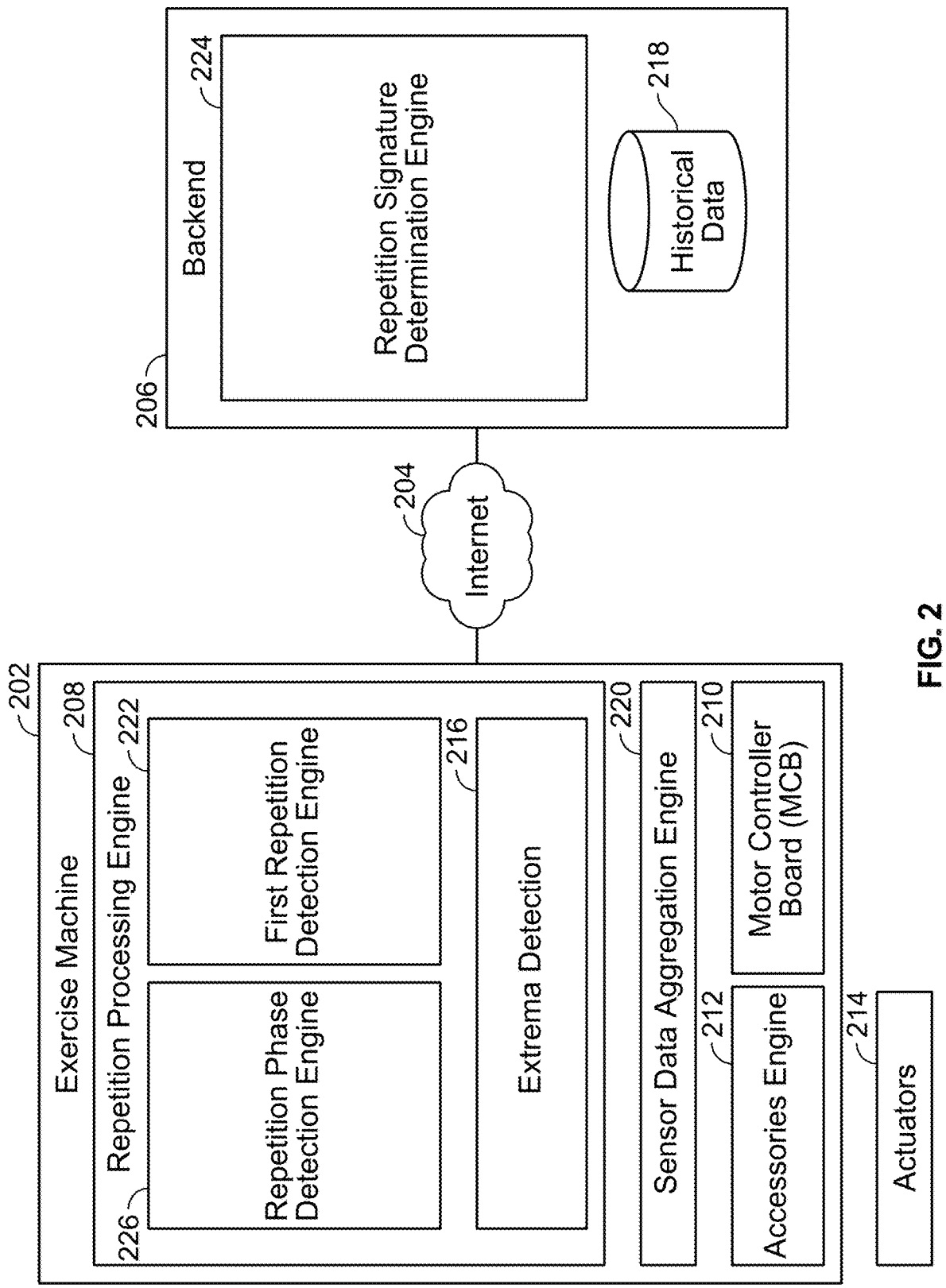
FIG. 2 illustrates an embodiment of a system for repetition analysis.

FIG. 2 illustrates an embodiment of a system for repetition monitoring and analysis. In this example, exercise machine 202 is an alternate view of the exercise machine embodiments shown in FIGS. 1A and 1B. As shown in this example, exercise machine 202 also communicates (over a network 204 such as the Internet) with backend 206. For illustrative purposes, examples involving a digital strength trainer with two arms are described.

In this example, exercise machine 202 includes repetition processing engine 208, motor controller board 210 (an example of motor controller 1004), accessories engine 212, and actuators 214. In some embodiments, these elements are compute/sensor nodes that form a computation architecture/stack in which sensor measurements are taken, and computations on such sensor measurements are made, at various levels.

In this example, at the bottom level/layer of the stack are actuators/accessories 214, examples of which include handles, bar controllers, smart mats, etc. In some embodiments, the sensors at the level of actuators 214 include IMUs, buttons, force sensors, etc.

At the next level of the computation architecture is accessories engine 212. Accessories engine 212 is configured to aggregate sensor data from the actuators. As one example, accessories engine 212 is implemented using the BLE (Bluetooth Low Energy) Central plugin, which communicates with accessories (e.g., via BLE, USB, RF, etc.). In some embodiments, the accessories engine is configured to determine the positions of accessories/actuators in physical space.

At the next level of the computation stack is motor controller board (MCB) 210. MCB 210 is another example of a computation node/layer in the computation architecture. In this example, the motor controller board collects data such as cable position and speed, motor position and speed, cable tension, scalable stack information (e.g., health of the motor, board, processor/memory of the board, and communication), etc. As one example, the motor controller board (MCB) is configured to receive encoder messages and determine right and left cable lengths. In some embodiments, the MCB provides such sensor readings to sensor data aggregation engine 220. The information may be sent via a communication bus such as a USB (Universal Serial Bus). The information may be sent periodically (e.g., at a frequency of 50 Hz).

In the next layer of the computation architecture is repetition processing engine 208. In some embodiments, repetition processing engine 208 is a portion of an exercise application running on a computing device included or otherwise associated with the exercise machine. As one example, the application is an Android application running on a computing device such as an Android tablet or computing device embedded in the exercise machine. In this example, repetition processing engine 208 is configured to detect a first repetition of a set, detect phases of repetitions, and control the exercise machine by processing and analyzing sensor data (e.g., from accessories and the MCB), as well as user data stored in user data store 218 (e.g., user profile, measurements, goals, suggested weights, etc.), workout data (e.g., current move, aggregate muscle utilization, movement attributes such as one or two-sided, etc.), camera and microphone information, etc.

As will be described in further detail below, repetition processing includes determining whether sensor readings are indicative of a first repetition having been performed by a user of the exercise machine. Repetition processing further includes determining phases of a repetition (e.g., what phase of a repetition a user is in). As will be further described in detail below, the repetition processing is determined based on a stream of measurements collected by various sensors of the exercise machine.

As shown in this example, the exercise machine is in communication (over a network 204 such as the Internet) with backend 206. As will be described in further detail below, in some embodiments, detection of a first repetition is based on matching a characterization of a stream of sensor measurements against a predetermined signature or pattern of motion. In some embodiments, the predetermined signature is obtained from or provided by backend 206. In some embodiments, sensor measurement data collected by the exercise machine (and from other client exercise machines) is included in information provided to backend 206, which is configured to store such information from client exercise machines in historical data store 218.

The next layer of the computation architecture includes backend 206. In this example, the backend compute node includes user data store 218, which includes information aggregated from multiple users of multiple exercise machines, and includes, for example, population statistics for all or subsets of users. In one embodiments, backend 206 is implemented on Amazon EC2 instances.

As shown in this example, data and data streams, such as sensors and user information/preferences, are distributed throughout the system/computation architecture.

In some embodiments, repetition processing (such as first repetition detection and repetition phase detection) is performed based on data collected from multiple sensors. Data may be fused, correlated, or analyzed at any compute node in a process referred to herein as "sensor fusion." The sensor data may also be passed through or pushed downwards to be operated on by various compute nodes in the computation stack.

As one example, suppose that the actuators 214 being used are two handles. The measurements taken from sensors (e.g., IMUs) in the two handles are passed to accessories engine 212 of the exercise machine, which aggregates, for example, sensor readings from all actuators. The actuator sensors data is then passed to repetition processing engine 208.

Sensor information collected by MCB 210 is also passed to sensor data aggregation engine 220. As shown in this example, sensor data aggregation engine 220 is configured to collect and aggregate the various and disparate sensor information (e.g., IMU sensor data, cable/motor/tension sensor data, etc.). Repetition processing engine 208 is then configured to detect the first repetition of a set and repetition phases using the combined sensor data.

In some embodiments, data, such as workout data (e.g., from MCB 210) and accessory data (e.g., smart bench data), is provided to backend 206.

In various embodiments, repetition processing and sensor data fusion are calculated at any of the above compute nodes in the computation architecture. In some embodiments, the algorithms and logic to perform the aforementioned repetition processing and sensor data fusion are distributed across the entire stack with interfaces between each to obtain optimal performance and accuracy, along with low latency. For example, tasks that require latency that is lower than is possible based on communication between layers are done at lower levels. When latency can be higher or when data is taken in aggregate (e.g., across an entire workout), algorithms are run at higher levels where more computational power and contextual data is available.

Further details regarding first repetition detection and detection of repetition phases are described below.

Detecting the First Repetition

First repetition detection engine 222 is configured to detect performance by a user of the first repetition in a set. As will be described in further detail below, the first repetition is detected by matching, against a previously determined signature, an extremum parameter of a detected extremum that is determined based on a characterization of a stream of measurements of an extension of a component of the exercise machine. Using the techniques described herein, the first repetition of a movement may be accurately detected and counted in real-time.

In the following examples and embodiments, detection of a first repetition when performing a bicep curl movement using a digital strength trainer is described for illustrative purposes. The first repetition detection techniques described herein may be variously adapted to detect a first repetition of any other exercise or movement as appropriate.

In the example of a bicep curl, the repetition starts at a minimum, not a maximum. As will be described in further detail below, the first repetition detection techniques described herein may be variously adapted to accommodate movements that start at a maximum rather than a minimum.

Obtaining Sensor Measurements

In this example, sensor readings are received, in real-time, by sensor data aggregation engine 220. As described above, in some embodiments, the sensor readings are received periodically (e.g., 50 times a second or at 50 Hz). Each sensor reading is also associated with a corresponding timestamp.

In some embodiments, the stream of measurements that are received is associated with the extension of a component of the exercise machine. For example, the sensor readings include cable measurements taken as the cable extends and retracts as the user moves a handle (or other actuator) of the exercise machine through a range of motion for the exercise. In the example digital strength trainer of FIG. 1B, the digital strength trainer includes two arms, each with a respective cable. In some embodiments, the cable measurements include cable lengths for the left and right cables, independently. In some embodiments, the sum of the two cable lengths is received. The sensor readings also include cable speed as well, for each cable.

The cable length sensor measurements may be obtained from encoders, such as those described above. For example, the exercise machine may include an encoder that determines motor rotation. The cable length may be determined by using the rotation of the motor and the spool size to determine how much the cable has extended or retracted. In other embodiments, the exercise machine includes an encoder that directly measures cable length and position. In some embodiments, the cable length (amount of extension) is measured relative to a cable "zero" point. One example of a cable "zero" point is the position of the handle when the cable is fully retracted (e.g., the handle is up against a ballstop at a wrist of the arm, and the cable cannot be retracted any further into the exercise machine).

Filtering

In some embodiments, filtering is performed on the stream of sensor readings. The filtering includes discarding certain samples based on certain conditions. This is because some of the sensor readings may include bad data. An example of a sensor reading that is filtered out is one that has a timestamp in the future and jumps ahead in time. As another example, there may be rollover in timestamps, causing them to go backwards (e.g., because a clock may be implemented as an integer that rolls over after the exercise machine has been left on for a long duration of time).

As another example, sensor readings where the length of a cable is out of bounds or is at a predetermined threshold are filtered out. As another example, duplicate samples are filtered out. In some embodiments, a queue of the last several (e.g., last 5) timestamps is maintained to identify duplicates (where one sample might not be a duplicate of the immediately previous sample, but a duplicate of the sample from two samples ago, or four samples ago). In some embodiments, two samples are determined to be duplicates if they have the same timestamp. If two samples are received that have the same timestamp, then one of the samples is discarded.

In some embodiments, the repetition detection algorithms (for detecting a first repetition and/or detecting phases of repetitions) described herein do not assume regular time samples, thereby handling missed samples (that is, the repetition detection algorithms described herein work with arbitrary time sampled data).

In some embodiments, sensor reading samples are logged. As one example, the samples of sensor readings are logged in a file such as CSV (comma separated values) and are then stored (e.g., uploaded to a backend such as Amazon S3). By logging sensor reading samples, the repetition detection algorithms described herein may be rerun on historical sensor reading samples. New repetition detection algorithms may also be trained on the historical sensor reading samples.

Extrema Detection

In some embodiments, the detection of the first repetition is based on detected extrema. Extrema detection engine 216 is configured to characterize the (filtered) stream of sensor measurements. The characterization includes detecting extremum having at least one extremum parameter. For example, the filtered sensor samples are evaluated to detect local maxima and minima of the cable position. In some embodiments, the cable position refers to the amount that the cable is extended from the arm. As one example, the "zero" position of the cable is when the handle or actuator is touching the "wrist" of the arm (and the cable is retracted as much as it can be). The cable position refers to the length or amount of the cable that has been pulled out relative to this "zero" point. As will be described in further detail, the detected local maxima and minima are then used to perform repetition detection.

In this example of performing a bicep curl, a necessary but not sufficient condition for a repetition to be determined to have occurred is that a cable minimum position (minimum position in the range of motion/positions for the move), followed by a cable maximum position (maximum position in the range of motion/positions for the move), followed then by a minimum is observed. If the stream of measurements can be characterized in this way, this indicates that this cable traversal path was followed.

As will be described in further detail below, in some embodiments, characterizing the (filtered) stream of sensor measurements includes taking detected extrema and determining whether the detected extrema follow the pattern of a repetition. Determining whether the pattern of a repetition has been followed by the detected extrema may be used to further filter out spurious minima and maxima that occur (e.g., because the user just stopped in the middle of a movement, lowered a bit, and then kept on going).

The following are examples of cable position-based and cable velocity-based extrema detection.

Cable Position-Based Extrema Detection

The following is an example of a cable length/position-based algorithm for detecting extrema. In this example, an exponential moving average of the cable length is determined. This exponential moving average lags the true cable length signal (e.g., cable length/position based on real time sensor readings). That is, if the exponential moving average and the real signal were plotted, the real signal would be ahead of the exponential weighted average in time.

In one embodiment, determining an extremum includes determining when the exponential weighted average of the cable length becomes within a threshold distance of the true cable length signal, with a buffer. That is, there is a crossover with a buffer.

Figure 3A:
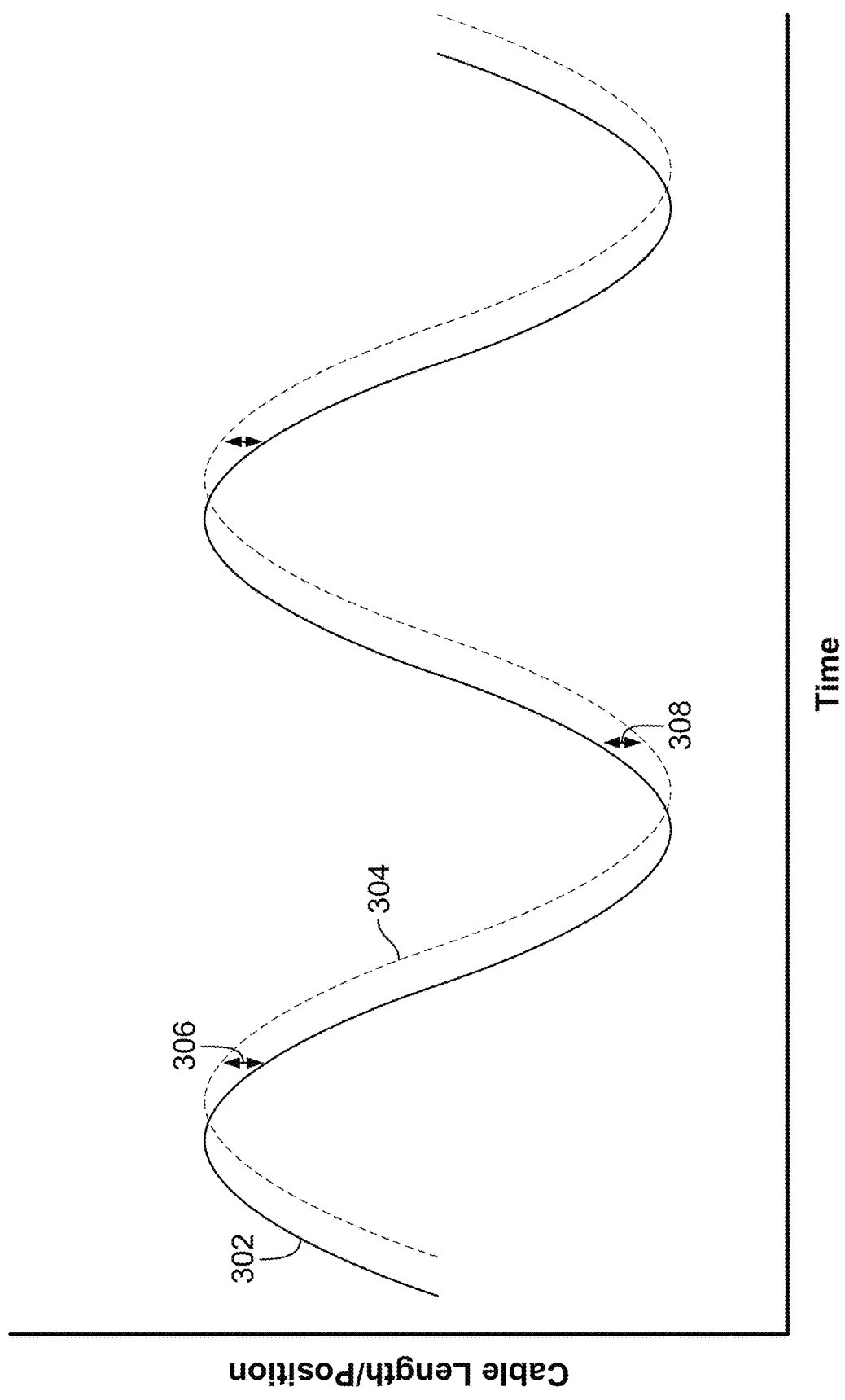
FIG. 3A is a diagram illustrating an embodiment of determining extrema.

FIG. 3A is a diagram illustrating an embodiment of determining extrema. In the example plot of FIG. 3A, the Y-axis is values of the true cable length (solid line 302) and values of the exponential weighted average cable length (dashed line 304), which are plotted over time (X-axis), As shown in this example, the exponential weighted average lags behind the true cable length signal, where the true data's maxima and minima (peaks and troughs) occur before the maxima and the minima of the exponential weighted average.

In some embodiments, to determine extrema, the difference between the exponential weighted average and the true signal is determined. If the difference between the exponential weighted average and the true signal is below a threshold, then it is determined that an extrema (max or min) has occurred.

In some embodiments, the sign of the difference is used to determine whether a max or min has occurred. For example, if the difference is calculated by subtracting, at a given time, the real signal from the exponential weighted average, where the difference is a positive value, and the absolute value of the difference is below a threshold, as shown at 306, then it is determined that a maximum has occurred.

As another example, if the difference is calculated by subtracting the real signal from the exponential weighted average, where the difference is a negative value, and the absolute value of the difference is below a threshold, as shown at 308, then it is determined that a minimum has occurred.

While in the above examples, the real signal was subtracted from the exponential weighted average, the reverse may also be computed, where the difference is determined by subtracting the exponential weighted average from the real signal. In this case, where the difference is determined by subtracting the exponential weighted average from the real signal, a maximum is determined when the difference is a negative value, and the absolute value of the difference is below a threshold. A minimum is determined when the difference is a positive value and the absolute value of the difference is below a threshold.

As shown in this example, an extremum such as the minimum is detected later than the occurrence of a maximum in the true cable length signal. This increases the confidence that the user has actually reached a maximum. In some embodiments, in response to detection of the extremum, various actions are triggered. For example, if a maximum is detected, then an eccentric weight mode is turned on. In some embodiments, the extremum detection is configured such that the extremum detection algorithm is faster at detecting minima than maxima.

Cable Speed-Based Extrema Detection

The following is an example of a cable speed-based algorithm for detecting extrema. In this example, a (motor and/or cable) speed/velocity-based extrema detection algorithm is described.

In this example, the exponentially smoothed moving average of the speed of the cable and/or motor is evaluated against the exponentially weighted average of the standard deviation of the speed of the cable and/or motor. For example, the speed of a motor and/or speed of the cable (measured, for example, as change in cable position/length over time, such as inches per second of the cable) is obtained from the stream of sensor reading samples. In this example, the cable speed is smoothed using an exponentially weighted mean. The exponentially weighted standard deviation of the cable speed is computed. In this example, when the exponentially weighted mean of the speed intersects the exponentially weighted standard deviation of the cable speed from above, a maximum is detected. When the exponentially weighted mean of the cable speed (change in cable length over time) intersects the exponentially weighted standard deviation *−1 from below, a minimum has been detected. Such detection of the maxima and minima is exemplified in the illustrative plot of FIG. 3B.

The following are four example parameters for a cable speed-based extrema detection algorithm.
1. Span for moving average (exponentially weighted average) used to smooth the (cable) speed.
2. Span for exponentially weighted standard deviation.
3. Coefficient for the standard deviation. This factor used to multiply the standard deviation may be tuned, and may be used to increase the speed of detection of minima, but which may cause an increase in false positives. In some embodiments, this coefficient is split into two, one for maxima detection, and a different coefficient for minima detection, for independent tuning of each coefficient.
4. Minimum value of the standard deviation. In some embodiments, this parameter is split into two, one for maxima detection and a different one for minima detection, for independent tuning.

Figure 3B:
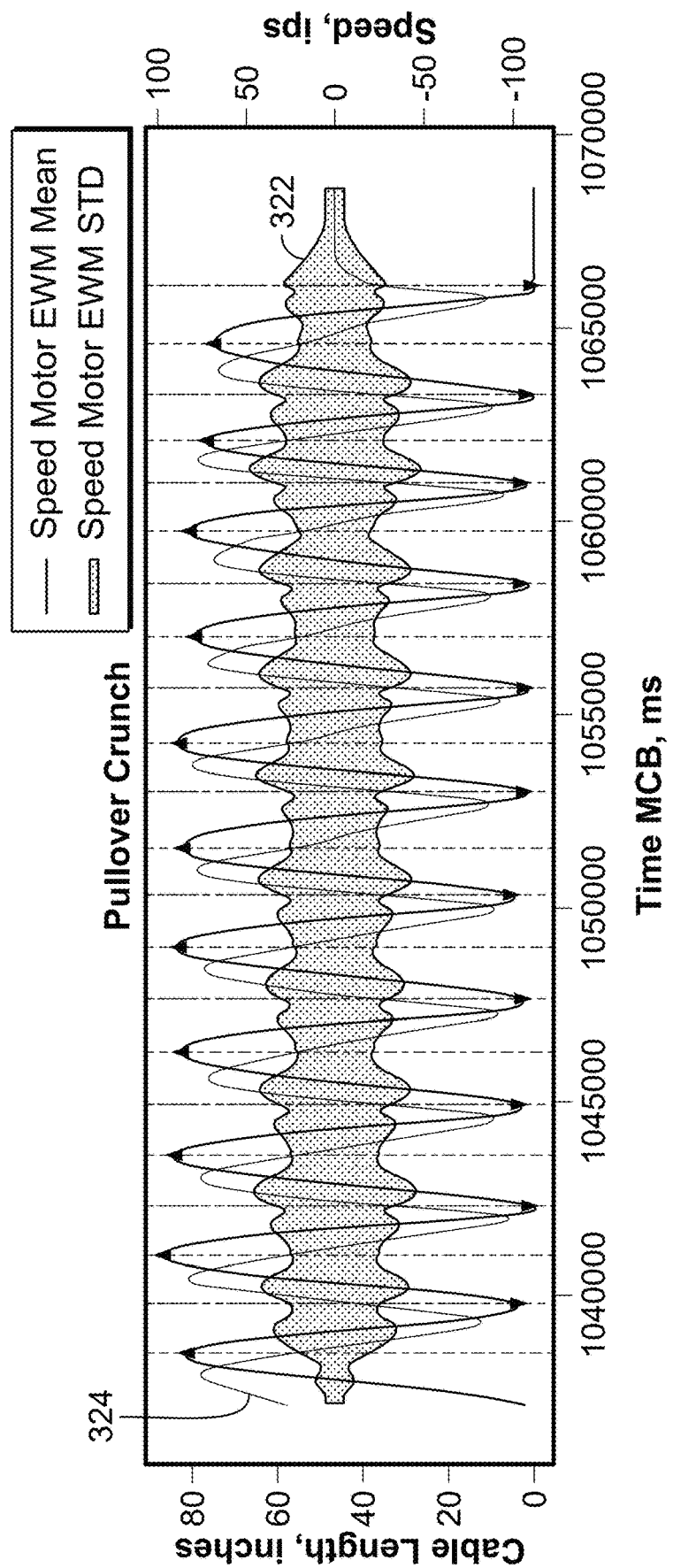
FIG. 3B is an embodiment of a plot.

FIG. 3B is an embodiment of a plot. In this example, the values of the exponentially smoothed average speed and the exponentially weighted average of the standard deviation (Y-axis) are plotted over time (X-axis). In this example, the exponentially weighted average of the standard deviation is shown at 322. The exponentially weighted average of the speed is shown at 324.

In this example, a maximum is detected when the exponentially weighted average of the speed crosses into, from above, the exponentially weighted average of the standard deviation. In this example, a minimum is detected when the exponentially weighted average of the speed crosses into, from below, the exponentially weighted average of the standard deviation.

Using the exponentially weighted average of the standard deviation, as described herein, noise and spurious motions are better rejected, where the more the cable speed signal fluctuates, the longer it takes to trigger detection of an extremum. For example, when using the true cable velocity signal, if the true signal is noisy, this may result in extremum false positives being detected (e.g., an extremum being flagged as having been detected, even though an extremum did not actually occur or was not intended). Here, in this example, by using exponentially weighted standard deviations, the detection algorithm is not disrupted by any single noisy measurement in the true cable velocity signal.

In this example, the maximum or minimum is detected before the exponentially weighted average velocity switches sign. This signal lags the true velocity in time, so the true velocity has likely switched signs while the exponentially weighted average velocity has not yet changed signs.

In some embodiments, the cable positions at the detected extrema are recorded as the minima/maxima.

Detecting the First Repetition

As shown in the above examples, extrema are detected from the stream of sensor measurements and readings. In some embodiments, the pattern or timing of the extrema of the user's current motion are matched against a previously determined repetition signature for the user for the exercise. If a match is detected, then a first repetition has been detected.

For example, in some embodiments, a candidate repetition is detected by determining a pattern or sequence of extrema having occurred (e.g., of a maximum, minimum, then a maximum having occurred; or a minimum, then a maximum, then a minimum, depending on the type of movement).

In some embodiments, a timing constraint is applied to the sequence of extrema before it is considered a candidate repetition. For example, if the time between a minimum and a maximum is below a minimum time requirement, then it is determined that the motions should not be considered a candidate repetition. As another example, it is determined whether a time between extrema exceeds a threshold time requirement. For example, when detecting a first repetition in real time, if the amount of time that passes between two extrema exceeds a threshold, then the sequence of extrema is determined to be not a repetition.

In some embodiments, in order to determine whether this candidate repetition should be counted as a first repetition, the pattern of the candidate repetition is compared against a predetermined repetition pattern (that was determined prior to the current set being performed).

The following are embodiments of obtaining the signature determined using historical data, where the signature is compared against the sequence of extrema determined from the real-time stream of measurements.

In some embodiments, a computing node (e.g., first repetition detection engine 222 of exercise machine 202 of FIG. 2) is configured to make a request (e.g., API Application Programming Interface request) to a backend (e.g., backend 206) to obtain historical measurement data associated with the user. In some embodiments, the requests are sent at the beginning of every set. In other embodiments, the requests are sent at the end of the previous set.

In some embodiments, the user performs movements according to a workout timeline generated by the exercise machine. In some embodiments, the timeline indicates when a movement has now switched. In some embodiments, at that time, and before the next set begins, repetition detection parameters (e.g., the allowable ranges of cable position max/min) are obtained from the backend for the next movement (which as described above, are based on the historical data collected for the user up that point). In some embodiments, suggested weights for the next movement are also obtained from the backend. In some embodiments, the repetition detection parameters are obtained mid workout and are cached.

In this example, the backend returns acceptable ranges of minimum and maximum positions for the cable length, which may vary by movement. In some embodiments, the acceptable range for an extremum is defined as a value for the extremum, along with an allowed percentage variation. For example, some moves may have a very narrow acceptable range. Different amounts of variation are allowed (e.g., in the acceptable ranges of max/min cable length positions) depending on the move. This may be due to the different amounts of natural variation that may occur. For example, if the exercise being performed involves standing, then the user may stand closer or further from the machine, and more variation may be allowed. On the other hand, when a user is laying on a bench to perform a bench press, and the user should be operating within a certain range of motion, the variation allowed may be lower. In some embodiments, the range of motion of the user (which may vary from repetition to repetition) is defined by the minimum and maximum cable lengths observed as part of the range of motion when the user performs a movement. For example, if the minimum cable length is 20 inches, and the maximum cable length (the maximum amount that the cable was pulled out relative to the "zero" point described above during performance of the exercise) is 50 inches, then the range of motion is defined to be the difference, 50 inches−20 inches=30 inches.

After the acceptable ranges of max and min cable positions are obtained (or similarly, max position and range of motion), a pattern is searched for in the user's current motions (e.g., in the user's current performance of a movement during the current set), which includes determining whether minima/maxima occur in a sequence that matches the conditions (acceptable ranges of max/min cable positions defined in the first repetition detection parameters). If a match is determined, then the user's motions in performing the movement are counted as a first repetition. If the user's motions are outside of the boundaries, then a repetition is not counted.

Thus, as described above, a repetition detection signature is determined using historical data (both global information across a user base, and information pertaining to the specific user). This historical data is used to determine a personalized maximum and minimum for a user for the movement, as well as a percentage variation that is allowed. This defines the boundaries of an acceptable range of max/min of cable position when identifying range of motion extrema.

As shown in the examples above, prior to a set beginning, the repetition detection signature including the repetition detection parameters is obtained. When the user starts to perform a movement, a stream of measurements (including samples of sensor readings) is received. An extrema detection algorithm, such as those described above, is used to detect maxima and minima in the user's current range of motion. The sequence of maxima and minima in the user's current motion is compared or matched against a predetermined sequence of max/min and the repetition detection parameters are used to detect whether a first repetition has occurred (that is, in some embodiments, in addition to determining that a certain sequence (in a certain order) of extrema has occurred, the extrema must also be within the boundaries defined by the repetition detection parameters in order for the first repetition to be determined to have occurred).

In some embodiments, based on detection of the first repetition, output of the exercise machine is changed. For example, if the first repetition is detected, then a repetition counter is incremented (e.g., from 0 to 1). In some embodiments, incrementing of the counter is indicated to the user. The indication of the counting of the first repetition may be performed in a variety of ways, such as visually (e.g., displayed on a screen associated with the exercise machine), acoustically (e.g., via a speaker associated with the exercise machine), or in an audiovisual manner (e.g., displayed visually and outputted via a speaker).

Other actions triggered off of detecting the first repetition include updating metrics about the workout such as average power, work, volume load (reps*weight), calories burned, distance covered, and pace (seconds/rep). Another example set of actions triggered includes detecting and indicating good form or types of bad form that could decrease effectiveness or increase injury risk. Another set of actions triggered includes controlling dynamic weight algorithms, including increasing or decreasing the weight to increase the effectiveness of training such as increased resistance in the eccentric phase, varying weight as a function of the percentage of the range of motion, or reducing the weight slightly to help the user complete the rep ("spotting"). Another example triggered action is dynamic audio and video that is reactive to the user, such as showing a video of an instructor giving instructions until after the user completes the first repetition. Another example triggered action is being entered into social and community experiences such as a leaderboard with other users who are lifting at the same time or who performed this exercise and workout in the past (asynchronous social interaction).

In some embodiments, repetition data collected for a repetition is saved. The repetition data, which may vary for each repetition that is performed, includes the maximum cable position for a given repetition, the minimum cable position for the given repetition, and the range of motion for the given repetition (e.g., the difference between the minimum cable position and the maximum cable position, where the minimum cable position and the maximum cable position are the lower and upper bounds, respectively, of the range of motion). Average range of motion, average minimum cable position, and average maximum cable position across all repetitions in the set are also computed. In some embodiments, the various repetition data is provided to a backend. The repetition data may be stored to a record associated with the user, and may be used to update the repetition detection parameters for the user (e.g., update the personalized maximum and minimum cable positions for the user).

The following are further details and embodiments regarding detection of a first repetition of an exercise.

Determining Repetition Detection Parameters

As described above, repetition detection parameters are received that are based on historical exercise information. The following are further details regarding the generation of repetition detection parameters. In some embodiments, the repetition detection parameters of the repetition signature are generated by repetition signature determination engine 224 of backend 206 of FIG. 2.

In some embodiments, historical sets for users over time are evaluated to determine the amount of variation in maxima/minima. In some embodiments, the historical data is evaluated across a global pool of users (where in some embodiments, such global user data is collected by backend 206 from multiple client exercise machines such as exercise machine 202, and stored in historical data store 218). In some embodiments, the percentage change from a user's own data is evaluated. As one example, the max position for each user is normalized. The percentage change for each user is then checked. A histogram is then determined of how far away the user was from their average (e.g., in percentage terms).

In some embodiments, the percentage of variation allowed (e.g., range) is not personalized. However, the values of the maximum and minimum defined in the repetition detection parameters of the signature are personalized. That is, in some embodiments, the range of allowable max/min positions is defined as a personalized maximum and minimum, along with a percentage variation allowed (where the percentage variation is computed from an analysis of historical information across multiple users).

The signature maximum and minimum values may be determined based on a user's own previous sets. In some embodiments, the percentage variation is fixed or consistent across users for a given move (as most users may be fairly consistent in how much variation they had). In some embodiments, each movement is handled separately, where the amount of variation for min/max is determined for each movement. In some embodiments, percentiles, such as $10^{th}$ to $90^{th}$ percentile of the amount of variation for min/max, are selected as acceptable boundaries.

Handling Movements that Start in Different Positions

As described above, detecting a first repetition in real time includes determining whether a detected sequence of extrema is in a particular order. The particular order that the detected sequence should match may vary depending on movement. For example, some movements begin with the cable at the maximum end of the range of motion (i.e., cable is at its most extended for the range of motion). Other movements begin with the cable at the minimum end of the range of motion (i.e., cable is at its most retracted for the range of motion). For these different types of exercises, the ordering of extrema that should be observed for a repetition differs (e.g., the order should be min then max for one type of movement, and max then min for another type of movement). In some embodiments, the repetition detection parameters include a flag that indicates whether the movement to be performed has repetitions that start on a min or a max. Based on this flag, the repetition detection algorithm determines the appropriate ordering of extrema that extrema detected from the stream of measurements being actively collected should match.

Fallback/Default Repetition Detection

Another embodiment of detecting the first repetition includes retroactive counting of the first repetition after two matching repetitions have been detected in the current set. That is, before counting (and displaying the number of repetitions that have been performed), repeating of a same pattern twice is first detected before it is determined that repetitions have occurred. This technique may be used to ensure that certain movements are not accidentally counted as repetitions. For example, suppose that a user is performing a bench press, laying down on the bench, and moving the handles around. As the user is preparing to perform the bench press, the handles may move around greatly, where the detected motion may appear to be a repetition. In order to ensure that repetitions are counted correctly, in some embodiments, counting does not start until the same pattern of movement is observed twice. That is, the first repetition is retroactively counted.

For example, the first sequence of extrema and their values are maintained. If a second sequence of extrema follows that matches the first sequence, then it is determined the first sequence and the second sequence are both repetitions (that is, the user is firmly or unequivocally attempting to perform repetitions, as indicated by observing the user performing the same motions twice), and the counter is incremented (by two).

The sensor measurements associated with the pattern determined to be the first repetition are then used to calculate the various aggregate metrics described above to determine what occurred during those reps. Here, displaying to the user (e.g., on a screen associated with the exercise machine) of the completion of two repetitions (and incrementing of the repetition counter) does not occur until after two repetitions.

In some embodiments, if there is not a previous pattern (e.g., no historical data to use to determine a signature) to use to determine the occurrence of the first repetition, or if the current set of measurements fails to match to a predetermined pattern (e.g., the user's current pattern of motion falls outside of the boundaries defined by the repetition detection parameters described above), then the aforementioned technique involving detecting two matching patterns within the current set is performed as default and used to count repetitions (e.g., after detecting two matching patterns/sequences of extrema within a set of bounds having occurred). As another example, the aforementioned technique of detecting to matching patterns in the current set is used by default if the user has never performed the movement before.

Figure 4:
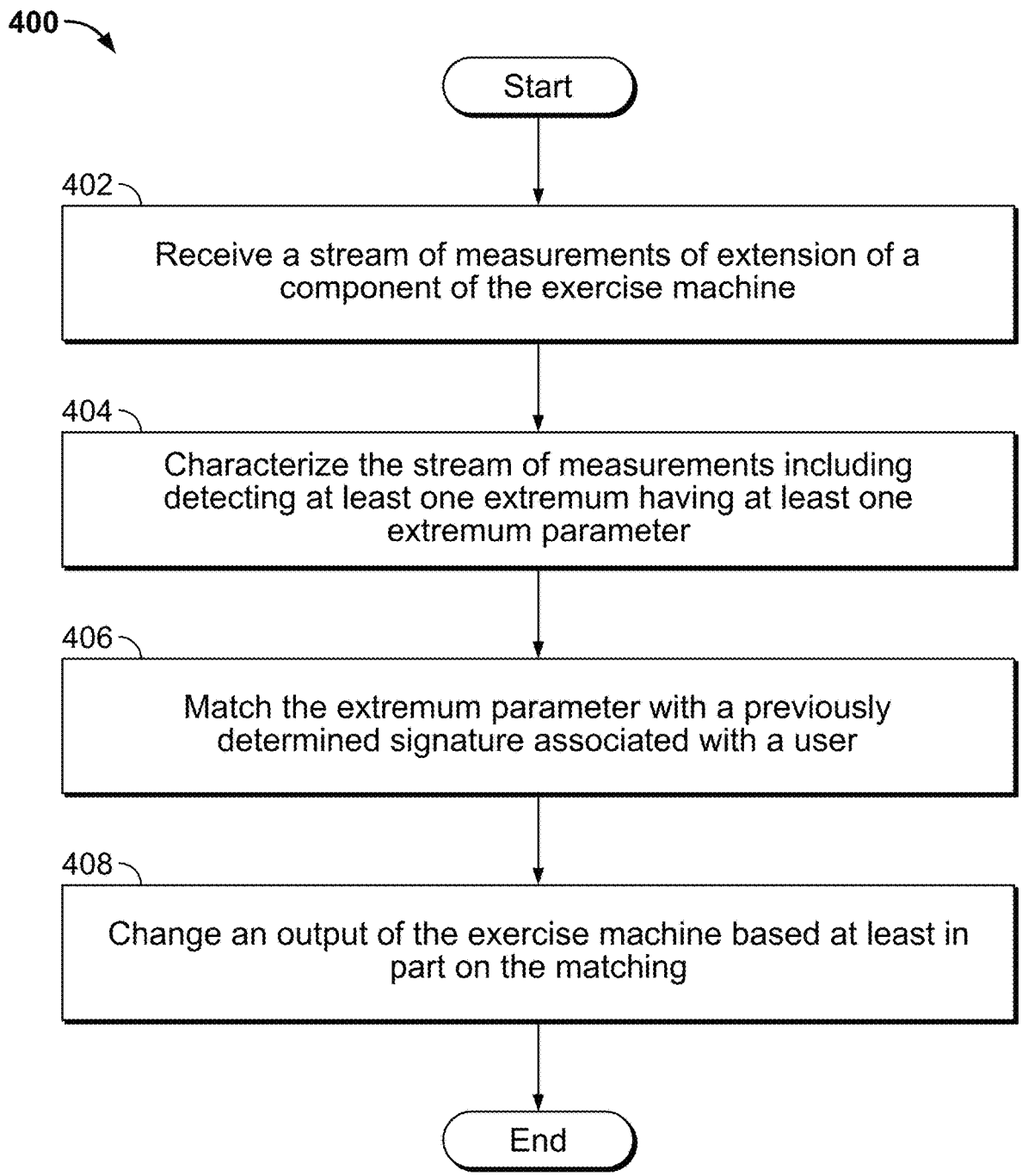
FIG. 4 is a flow diagram illustrating an embodiment of a process for controlling an exercise machine.

FIG. 4 is a flow diagram illustrating an embodiment of a process for controlling an exercise machine. In some embodiments, process 400 for controlling an exercise machine is based on detection of a first repetition. In some embodiments, process 400 is executed by first repetition detection engine 222 of FIG. 2. The process begins at 402, when a stream of measurements of extension of a component of the exercise machine is received. As one example, the stream of measurements pertains to the cable length, and the stream of measurements includes samples of the cable length over time. The cable length/position may be determined by an encoder, as described above.

At 404, the stream of measurements is characterized. Characterizing the stream of measurements includes detecting at least one extremum having at least one extremum parameter. One example of a parameter is how far the cable is extended. Examples of determining extrema are described above. In some embodiments, characterizing the stream of measurements includes filtering samples of sensor readings, as described above.

At 406, the extremum parameter is matched with a previously determined signature associated with a user. In some embodiments, the predetermined signature includes a set of repetition detection parameters for the user. For example, in some embodiments, performing the matching includes matching a length of extension. As another example, the matching includes determining that a maximum detected from the stream of measurements matches a previous maximum extension (e.g., within an acceptable range as defined in the predetermined signature). In some embodiments, constraints, such as the timing constraints described above, are used to disqualify a sequence of observed extrema from being considered as a repetition. If a match is found, then it is determined that a first repetition has been detected. Further details regarding repetition detection parameters and matching are described above.

At 408, an output of the exercise machine is changed based on the match. For example, a counter is incremented that indicates that the first repetition has been performed. The incremented counter may be displayed. The measured parameters of the first repetition may then be used to detect when subsequent repetitions in a set have been performed (e.g., where the process 400 is repeated, but with the parameters of the first repetition used as the repetition detection parameters to define range of motion and allowable ranges of extrema for subsequent repetitions in the set).

Detecting Phases of a Repetition

Described below are embodiments of detecting phases of a repetition. In some embodiments, repetition phase detection engine 226 is configured to detect phases of a repetition. The repetition phase detection techniques described herein may be used to go beyond determining when a repetition ends and starts, and may be used to determine information about what is occurring throughout the repetition. This includes determining, in real-time, as the user is performing the repetition, what phase of the repetition the user is in. As will be described in further detail below, using the techniques described herein, a repetition is categorized into four parts:

(1) a concentric phase, which corresponds to when a cable is being retracted.
(2) an isometric hold, which is when the cable is extended, but is not moving anymore (for example, at the top or the bottom of the repetition), where the isometric hold is between the concentric and eccentric phase of the repetition.
(3) an eccentric phase, which corresponds to when a cable is retracting.
(4) a resting hold, similar to an isometric hold, but is between repetitions, such as in a bicep curl, where the user is at the top or bottom of the repetition, resting or waiting, before beginning the next repetition.

Using the techniques described herein, the boundaries of the phases are accurately detected, and each of the four phases of a repetition is individually identified. As will be described in further detail below, timings of the phases/states of a repetition, the position of the cable when a user begins and ends each one of those states/phases, etc. are determined. Further, aggregate metrics about each phase of a repetition are determined, such as average speed, maximum speed, maximum power, average power, duration of a phase, the time at which the maximum speed occurred, the time at which the maximum power occurred, etc.

For illustrative purposes, the examples provided herein involve motions where there are 4 states. More complicated examples are also possible using, for example, the state machine formulation described herein, such as compound moves where at the end of the concentric state, another new concentric state begins, such as in an "X Pulldown to Tricep Extension", which is two moves (X Pulldown and Tricep Extension) blended together such that the end of the concentric state of X Pulldown is eventually followed by, possibly with intermediate Isometric Hold states, the start of the concentric state of Tricep Extension. That is, different types of state machines with different numbers of states as transitions may be used depending on what exercise is being performed.

Further, the phase detection techniques described herein are usable to detect the phase of repetitions for two classes of movements: one class of movement where the repetition starts at the bottom (e.g., where the repetition starts at the bottom, or minimum cable extension boundary, of the range of motion for the exercise), and one class of movement where the repetition starts at the top (e.g., where the repetition starts at the top, or maximum cable extension boundary, of the range of motion for the exercise). Examples of movements that start at the "top" include squats, lunges, and bench presses. For example, in a bench press, the user should start with the arms extended (and the cables are extended to the maximum end of the range of motion). Examples of movements that start from the "bottom" include deadlifts, bicep curls, and tricep extensions.

In some embodiments, a repetition counter (that counts the number of repetitions that have been performed) increments at the end of the concentric phase. However, a repetition of a movement does not necessarily end with the end of the concentric phase. On a bicep curl, for example, the repetition counter increments when the concentric phase is finished, but the repetition is not yet over. For the bicep curl, the repetition ends when the user returns the weight down (allowing the cable to retract, such that the virtual weight stack is at the bottom of the range of motion again). However, for squats, which are a common example of the other class of movement, the repetition starts at the top (e.g., with the cable extended to the furthest end of the range of motion, and the virtual weight stack at the top), and not the bottom. Thus, in this example, the beginning of a repetition of a squat corresponds to the start of the eccentric phase, which is first, the user goes down (and the cable retracts), the user goes back up (the user extends the cable), and the repetition counter increments at the end of the repetition.

Repetition phase detection engine 226 is configured to detect the phases of a repetition. In some embodiments, detecting/identifying the phases of a repetition is implemented by encoding the phases in a state machine. As the user performs a repetition, depending on the stream of measurements that are collected from various sensors in the exercise machine, the user transitions from one state of the state machine to another, corresponding to transitioning from one phase of a repetition to another. For example, the concentric phase has a corresponding concentric state in the state machine. For some exercises, if the user is in the concentric state and then leaves the concentric state, the next state that they are allowed to enter is the isometric hold.

The state machines and/or transitions may depend on the type/classes of movement that are being performed. For example, the state machines and/or transitions may depend on whether the movement starts on a minimum (bottom) or a maximum (top).

For example, consider the bicep curl, where the user starts with the cable position at the minimum end of the range of motion (where the cable is pulled out the least during the exercise). For a movement starting on a minimum, if the user leaves the concentric phase (e.g., by detecting a cable length maximum that fits within a set of conditions, as will be described in further detail below), then the repetition transitions from having been in the concentric phase/state to the isometric hold/state at the top of the repetition (analogous to a virtual weight stack being at its highest point away from the ground during the exercise). The user/repetition remains in that state until another set of conditions are met (e.g., that the cable length has decreased a certain amount or by a certain percentage range of motion, analogous to a cable retracting and a virtual weight stack returning back towards the ground), after which the user/repetition transitions out of the isometric phase/state and enters the eccentric phase. The user/repetition remains in the eccentric phase/state until a cable length position minimum is detected that meets a set of conditions/criteria, as will be described in further detail below. The repetition then enters a next resting state, waiting for the next repetition to begin. In some embodiments, the transition out of the waiting state occurs when the cable length extends a certain amount, at which point the concentric phase/state is returned to and entered.

Example State Machines

Figure 5A:
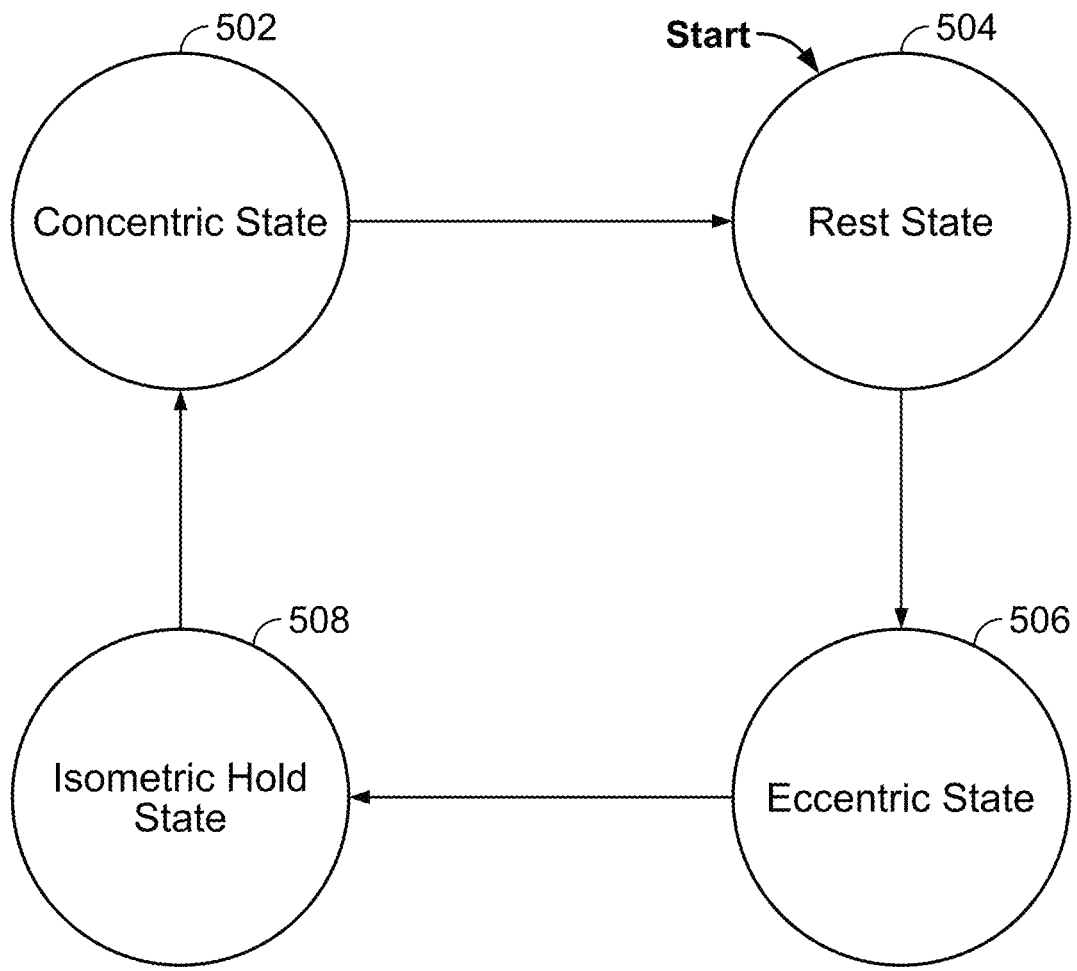
FIG. 5A illustrates an embodiment of a state diagram for repetition phases of movements that begin at the top.
Figure 5B:
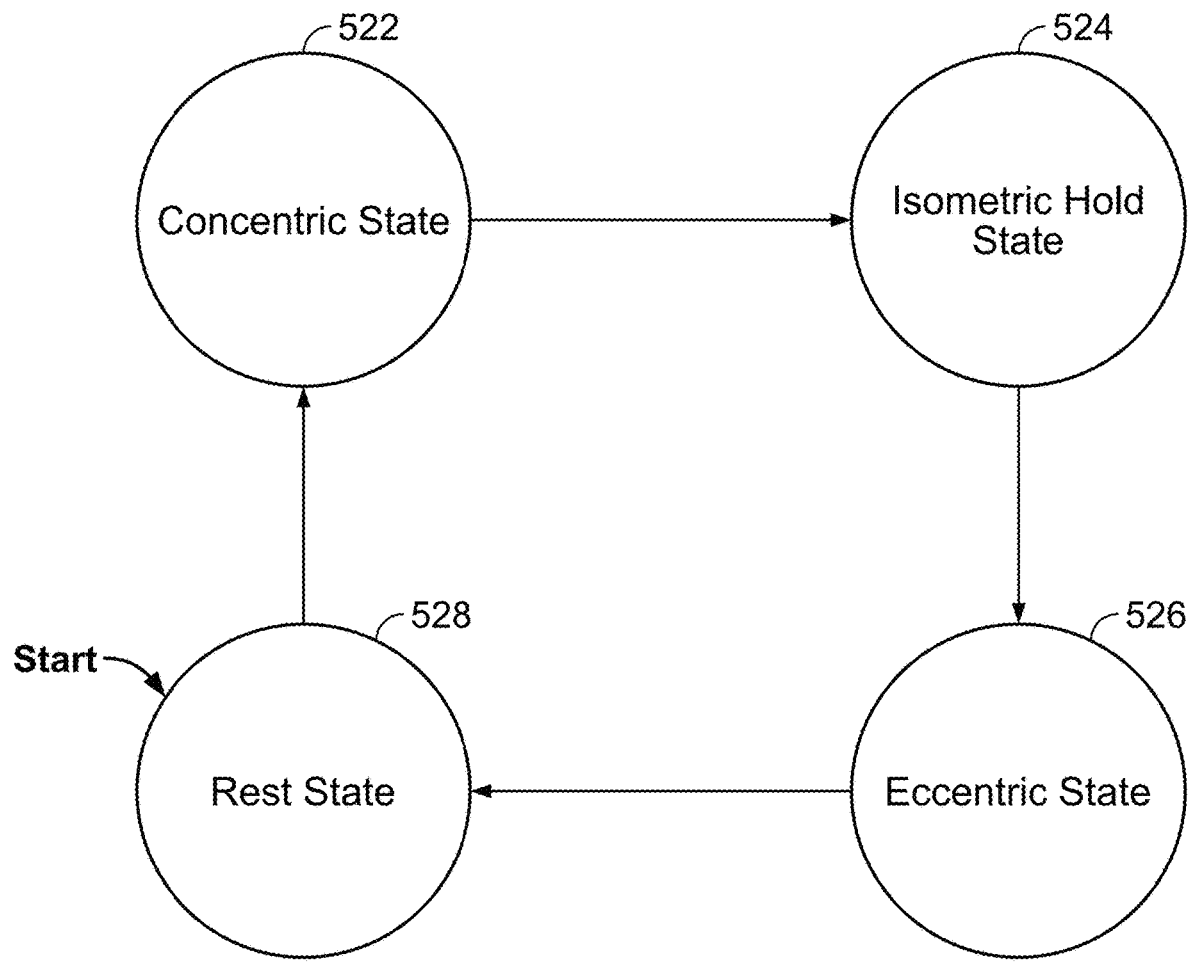
FIG. 5B illustrates an embodiment of a state diagram for repetition phases of movements that begin at the bottom.

FIGS. 5A and 5B illustrate embodiments of state diagrams corresponding to repetition phases.

Example State Machine for Top-Starting Movements

FIG. 5A illustrates an embodiment of a state diagram for repetition phases of movements that begin at the top. Examples of movements that begin from the top include squats, lunges, and bench presses. In some embodiments, beginning at the "top" refers to the starting position of the repetition corresponding to a "top" or maximum end of the range of motion (defined, for example, using cable length/position) for the movement. This corresponds, for example, to the repetition starting with a virtual weight stack further away from the ground.

In some embodiments, the initial state is the "rest" state, and occurs, for example, when the cable is both not grounded (not resting on the wrist) and the weight is turned on. The transitions from the rest state are different for the two classes of moves that start at the top and bottom of the range of motion, as described above, and as will also be described below in conjunction with the example of FIG. 5B.

Concentric State (502): In this example, in the concentric state, a valid maximum is monitored for. When a valid maximum is detected, then Rest state (504) is entered.

In some embodiments, the valid maximum is computed relative to the range of motion. For example, a rule is defined that specifies that a threshold percentage of range of motion (e.g., 65%) is required to have been covered before exiting the concentric phase into rest state.

Examples of aggregate metrics computed during the concentric state include maximum instantaneous power/speed, average speed, beginning/ending times of the concentric phase (e.g., timestamps for when the concentric state was entered/exited), force applied on the cables, work performed over the entire phase (integration of force times distance), a timestamp of when maximum power occurred, the cable length position at which maximum power occurred, a timestamp of when maximum speed occurred, the cable position at the time that maximum speed occurred, etc.

Rest State (504): In this example, in the rest state, a position decrease by at least a threshold amount is monitored for. When the position decreases by at least a threshold amount, then the eccentric state (506) is entered. In some embodiments, the rest state is a state during which the next rep is waited for. In some embodiments, the threshold is a function of range of motion (e.g., position change as a percentage or proportion of range of motion)

Eccentric State (506): In this example, in the eccentric state, a valid minimum is monitored for. When a valid minimum is detected, then the isometric hold state (508) is entered.

For example, the eccentric state 506 is exited when a suitable filtered minimum is detected. A suitable filtered minimum may be determined based on a threshold minimum cable position. The suitability may also be determined based on a timing constraint, such as a threshold amount of time having passed. The suitability may also be determined on range of motion (e.g., that a threshold percentage or proportion of range of motion has been covered since the last maximum).

Examples of metrics collected for the eccentric state include a max speed (e.g., absolute value, as the direction is negative since the cable length is shortening as the cable is retracting back into the machine during the eccentric phase), beginning and end times of the eccentric state (e.g., timestamps for when the state was entered, and when the state was exited), beginning and ending cable length positions, etc.

Isometric Hold State (508): In this example, in the isometric hold state, a position increase by at least a threshold amount is monitored for. When the cable position increases by at least the threshold amount, then the concentric state (502) is entered.

In some embodiments, the amount of time spent in the isometric hold state is computed. The amount of time spent in the isometric hold state may be computed in a variety of ways. As one example, the time spent in the isometric hold state is computed based on the timestamps recorded for entering and exiting the isometric hold state. As another example, the time spent in the isometric hold state is determined based on timestamps recorded for exiting of the previous state and for entering the next state.

Example State Machine for Bottom-Starting Movements

FIG. 5B illustrates an embodiment of a state diagram for repetition phases of movements that begin at the bottom (of the range of motion). Examples of movements that begin from the bottom include deadlifts, bicep curls, and tricep extensions. In comparison to the example of FIG. 5A, for a move that starts at the bottom, the rest and isometric hold states are reversed, and are switched between coming after concentric or after eccentric. In some embodiments, beginning at the "bottom" refers to the starting position of the repetition corresponding to a "bottom" or minimum of the range of motion for the movement. In some embodiments, this corresponds to the repetition starting with a virtual weight stack closer to the ground.

In some embodiments, the starting state is the rest state, similarly to as described above in conjunction with the example of FIG. 5A.

Concentric State (522): In this example, in the concentric state, a valid maximum is monitored for. When a valid maximum is detected, then Isometric Hold state (524) is entered. Examples of valid maxima and aggregate metrics include those described above in conjunction with concentric state 502 of FIG. 5A.

Isometric Hold State (524): In this example, in the isometric hold state, a position decrease by at least a threshold amount is monitored for. When the cable position decreases by at least the threshold amount, then the eccentric state (526) is entered. Examples of metrics computed during the isometric hold state are described above in conjunction with isometric hold state 508 of FIG. 5A.

Eccentric State (526): In this example, in the eccentric state, a valid minimum is monitored for. When a valid minimum is detected, then rest state (528) is entered. Examples of valid minima and aggregate metrics computed for the eccentric state are described above in conjunction with eccentric state 506 of FIG. 5A.

Rest State (528): In this example, in the rest state, a position increase by at least a threshold amount is monitored for. When the position increases by at least the threshold amount, then the concentric state (522) is entered. In some embodiments, the rest state is a state during which the next rep is waited for. In some embodiments, the threshold is a function of range of motion (e.g., position change as a percentage or proportion of range of motion).

In some embodiments, the repetition counter is incremented after the concentric phase is transitioned out of. In the case of the bicep curl, the first half repetition (which is the first concentric phase for the bicep curl) is monitored for, and when the first concentric phase is detected, and the conditions for a correct concentric phase of a repetition are met, then the repetition counter is incremented. In this example, when the repetition counter is incremented, only half of a repetition has been completed so far. That is, after having completed half a repetition (the concentric phase portion of the repetition), the counter is incremented, and the repetition enters the isometric hold phase/state.

In the case of a movement that starts from the top, such as the bench press, completion of the first two phases is monitored for, before incrementing the repetition counter (such that the counter is incremented after the concentric phase).

In some embodiments, the use of completion of the concentric phase as a trigger to increment the repetition counter increases the accuracy of repetition detection. This is in part because it is more difficult for users to have anomalous patterns of behavior when in the concentric phase. That is, the motions of the concentric phase are not typically performed unless the user is actively trying to perform their repetition.

In some embodiments, two separate state machines (for the two different positions, top and bottom, at which movements may start) are maintained, and one is instantiated at a time (depending on what movement the user is currently performing). In other embodiments, a single state machine is maintained, and the state machine logic (e.g., for transitions, triggers, starting states, etc.) is modified at runtime by passing in an indicator (e.g., a flag) that indicates the type of movement being performed (e.g., movement starting at top or movement starting at bottom).

In some embodiments, a phase detection state diagram includes a set of special states for monitoring for the first repetition. In the example of the bicep curl, sensor measurements are monitored for conditions to be met for the first concentric phase for the bicep curl (e.g., by looking for extrema to match within the acceptable ranges of repetition detection parameters, as described above). If those conditions are met, then a state corresponding to waiting for the first repetition to be detected is immediately left, and the isometric hold state is entered into.

In some embodiments, the special version of the "waiting for" state for the first repetition uses the predetermined signature described above to detect the first concentric phase of the first repetition. After the concentric phase of the first repetition has been detected (and the counter incremented), then the waiting for/rest state does not need to use the predetermined signature to determine the occurrence of the concentric phase. For example, the actual measurements collected during the performance of the first repetition are used for the remainder of the set. For example, the repetition phase detection algorithm/logic switches over to determining what the user's range of motion was for that first phase of the first repetition, which is then used to update thresholds and range of motion for detecting future phases of repetitions in the set.

In some embodiments, different actions are taken based on the phase of the repetition that the user is in. As one example, the resistance provided by the motor is adjusted or changed based on what phase of the repetition the user is in. For example, different amounts of load or resistance may be provided for the concentric and eccentric phases.

Another example action based on the state of the user is types of pacing guidance and feedback such as to move faster during the concentric state and slower in the eccentric state, to pause longer in the isometric hold, and reduce time in the rest state. Another example action is different visuals and metrics such as visualizing the instantaneous power or speed in concentric state but not in any other state.

Detecting Phase Boundaries

As described above, phase boundaries (e.g., when to exit/enter into certain phase states) are determined based on detected extrema. Extrema, such as maxima and minima, may be determined using extrema detection techniques such as those described above.

Removing Artificial Extrema

In some embodiments, debouncing is performed to remove bogus extrema. Such bogus extrema may occur naturally, as users may have a pause in the midst of performing certain kinds of movements. However, this pause or hitch does not necessarily indicate that the phase has switched. For example, suppose that there is a minimum then a maximum because a user did half of a repetition, then took a pause, and then continued to finish the repetition, resulting in two maxima. This should not be counted as two repetitions. Debouncing is performed to remove intermediate bogus maxima.

Other artificial extrema are filtered out or removed based on timing constraints. For example, another example of an artificial extremum that can occur is because the user did not complete the full range of motion or because not enough time has passed for the user to have physically completed a repetition (e.g., it may not be physically possible for a user to have gone from a maximum to a minimum in the recorded amount of time, and if such a case is detected, then the repetition is not counted, as it may be due to bad data or some other error). In some embodiments, in order for a phase to be determined as having been completed, a threshold amount of time is required to have passed within the phase.

Updating Range of Motion

The range of motion may be defined or updated a number of ways. In some embodiments, the range of motion is updated after each repetition or phase of a repetition, based, for example, on the extrema that are detected in the previous reps in a set. For example, after multiple repetitions have been performed, the range of motion for a current repetition is computed as the median of all of the previous repetitions (in the current set). In this example, each phase may have a new range of motion, where the range of motion is used to determine, as described above, when to exit/enter states.

Determining when a Set Ends

The following are example details of an end set detection algorithm for determining when a set ends.

In some embodiments, in the example digital strength trainer described herein, users may turn the virtual weight (e.g., resistance to the user's pulling of the cable provided by the torque of the motor countering the user's motion) on or off. The weight may be turned on or off in a variety of ways, such as via a touch screen input, via a voice command, via a button or other control located on the exercise machine, such as on the actuator or the frame of the exercise machine, etc. In some embodiments, the current set is ended once it is detected that the user has turned the digital weight off. In some embodiments, the next set is not begun until the user turns the digital weights back on.

As another example, a set is ended if the user decides to progress to a next exercise in a workout routine (e.g., by pressing a "play next" button or providing some other input indication to move on to a next exercise in a workout routine).

Another example user indication that a set is to end is when the user puts the actuator (e.g., handles) down (even without turning off the digital weight) and a threshold amount of time passes. In some embodiments, the entire set is ended.

In some embodiments, if the user is in the middle of a repetition when they decide to end a set, then incomplete/partially completed repetitions are discarded. For example, if a repetition counter is incremented, then the repetition (and its associated collected/computed metrics) is saved. However, if the repetition counter has not been incremented, then the information for the current partially completed repetition is not saved and is discarded.

In some embodiments, if the exercise machine infers from the user's actions (e.g., by turning off the digital weight, putting the handles down, etc.) that the user has stopped the current set, the exercise machine performs various actions, such as stopping counting of repetitions, advancing a workout program (e.g., audiovisual program), etc. In some embodiments, the corresponding portion of an audiovisual workout program that pertains to the current exercise loops until an indication to end the set is detected.

There may be a variety of conditions for detecting an end set and for when the exercise machine ends a set on behalf of the user. For example, if the user is doing repetitions in which the cable position is close to the cable zero position, if the user puts the handles down, this may be because the user is resting the handles down naturally as part of their natural motion, and not because of the desire for the set to end right away. In this example, the exercise machine, based on the type of exercise being performed (e.g., one that is close to cable position zero), and the type of potential end set indicator (e.g., putting handles down), waits a longer threshold amount of time before triggering the end of the set. The threshold amount of time to wait before triggering the end of the set may dynamically change and be different based on the conditions being detected and monitored for. For example, if the user has also already completed their repetition goal (e.g., as specified by the workout routine), then the end set is triggered more quickly. If the user has only performed a small fraction of the repetition goal (e.g., less than a threshold number of repetitions, or less than a threshold percentage of the repetition goal), then a longer amount of time is waited before triggering ending of the set (as it is assumed that the user is more likely to continue the current exercise).

Figure 6:
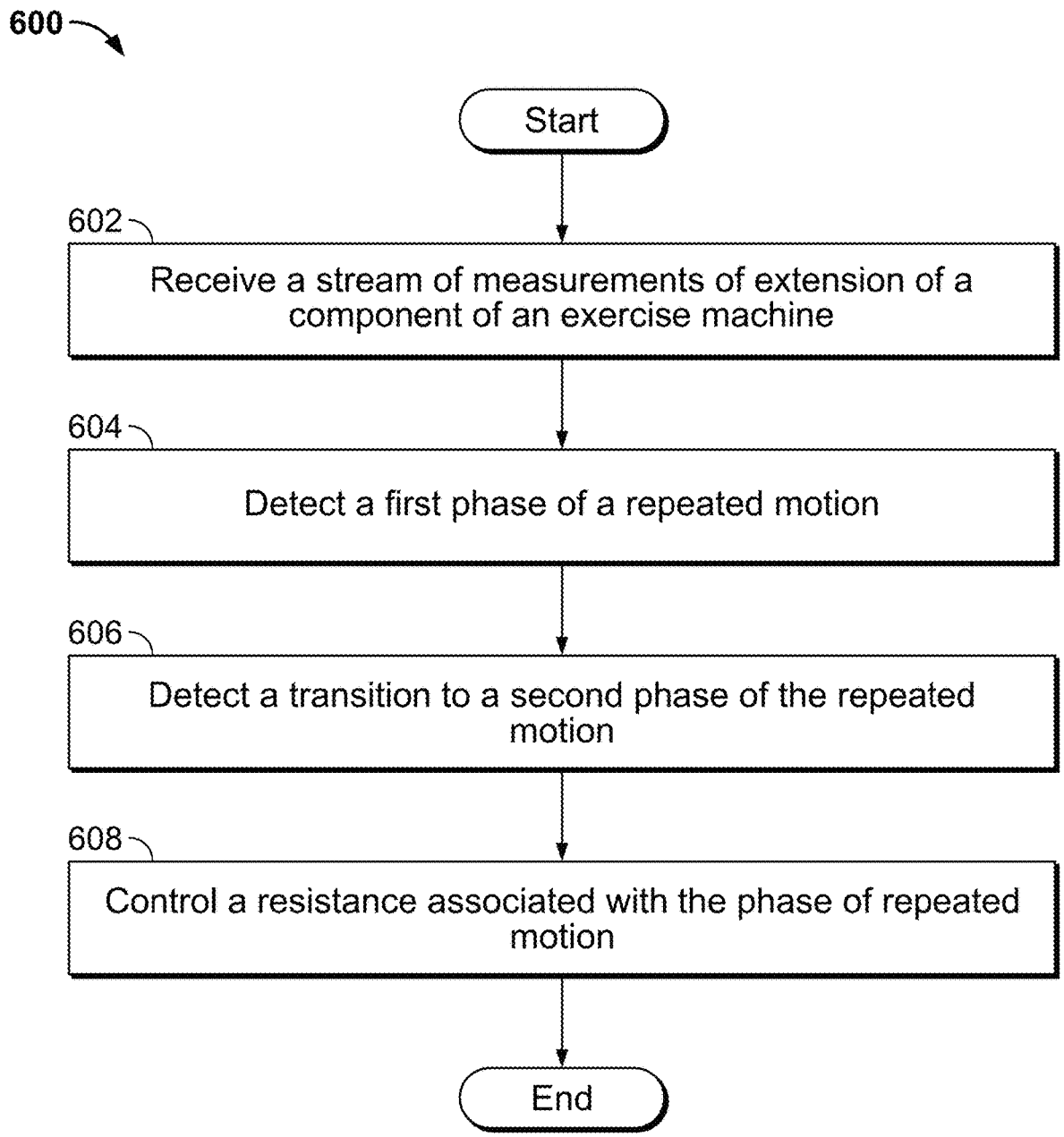
FIG. 6 is a flow diagram illustrating an embodiment of a process for controlling an exercise machine.

FIG. 6 is a flow diagram illustrating an embodiment of a process for controlling an exercise machine. In some embodiments, process 600 for controlling an exercise machine is based on detection of phases of a repetition. In some embodiments, process 600 is executed by repetition phase detection engine 226 of FIG. 2. The process begins at 602 when a stream of measurements of extension of a component of an exercise machine is received. As one example, the stream of measurements pertains to the cable length, and the stream of measurements includes samples of the cable length over time. The cable length/position may be determined by an encoder, as described above. At 604, a first phase of a repeated motion is detected. At 606, a transition to a second phase of the repeated motion is detected. A time constraint is applied to the detection of the transition to the second phase of the repeated motion. For example, the state machines described above are used to detect transitions between phases of a repetition. At 608, a resistance associated with at least one of the first phase or the second phase of repeated motion is controlled. In some embodiments, aggregate metrics for the first and/or second phases are determined. The aggregate metrics may also be stored. The aggregate metrics may also be sent to a backend. Further details regarding metrics computed for different repetition phases are described above.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
    a processor configured to:
        receive a stream of measurements of extension of a component of an exercise machine;
        detect a first phase of a repeated motion, wherein the repeated motion includes a squat, a lunge, a bench press, a deadlift, a bicep curl, a tricep extension, or any combination thereof;
        detect a transition to a second phase of the repeated motion, wherein a time constraint is applied to the detection of the transition to the second phase of the repeated motion, comprising to:

perform one of the following:
- A) determine that a position has changed by at least a first threshold amount while in a rest phase, wherein the first threshold amount is a function of a range of motion of the repeated motion; and
  - in response to a determination that position has changed by at least the first threshold amount while in the rest phase, detect that the transition has occurred;
- or
- B) determine that a position has changed by at least a second threshold amount while in an isometric hold phase, wherein the second threshold is a function of a range of motion of the repeated motion; and
  - in response to a determination that the position has changed by at least the second threshold amount while in the isometric hold phase, detect that the transition has occurred; and control a resistance associated with the second phase of the repeated motion; and a memory coupled to the processor and configured to provide the processor with instructions.

2. The system of claim 1, wherein the first phase comprises one of a concentric phase, the isometric hold phase, an eccentric phase, and the rest phase.

3. The system of claim 1, wherein the repeated motion is associated with an exercise that begins at a top position.

4. The system of claim 1, wherein the first phase comprises a concentric phase, wherein the second phase comprises the rest phase, and wherein the transition is detected at least in part by detecting a valid maximum.

5. The system of claim 1, wherein the first phase comprises a the rest phase, wherein the second phase comprises an eccentric phase, and wherein the transition is detected at least in part by detecting that a position of the component of the exercise machine has decreased by at least a third threshold amount.

6. The system of claim 1, wherein the first phase comprises an eccentric phase, wherein the second phase comprises the isometric hold phase, wherein the transition is detected at least in part by detecting a valid minimum.

7. The system of claim 1, wherein the repeated motion is associated with an exercise that begins at a bottom position.

8. The system of claim 7, wherein the first phase comprises an concentric phase, wherein the second phase comprises the isometric hold phase, and wherein the transition is detected at least in part by detecting a valid maximum.

9. The system of claim 7, wherein the first phase comprises the isometric hold phase, wherein the second phase comprises an eccentric phase, and wherein the transition is detected at least in part by detecting that a position of the component of the exercise machine has decreased by at least a fourth threshold amount.

10. The system of claim 7, wherein the first phase comprises an eccentric phase, the second phase comprises the rest phase, and wherein the transition is detected at least in part by detecting a valid minimum.

11. A method, comprising:
receiving a stream of measurements of extension of a component of an exercise machine;
detecting a first phase of a repeated motion, wherein the repeated motion includes a squat, a lunge, a bench press, a deadlift, a bicep curl, a tricep extension, or any combination thereof;
detecting a transition to a second phase of the repeated motion, wherein a time constraint is applied to the detection of the transition to the second phase of the repeated motion, comprising to:

performing one of the following:
- A) determining that a position has changed by at least a first threshold amount while in a rest phase, wherein the first threshold amount is a function of a range of motion of the repeated motion; and
  - in response to a determination that position has changed by at least the first threshold amount while in the rest phase, detecting that the transition has occurred;
- or
- B) determining that a position has changed by at least a second threshold amount while in an isometric phase, wherein the second threshold amount is a function of a range of motion of the repeated motion; and
  - in response to a determination that the position has changed by at least the second threshold amount while in the isometric phase, detecting that the transition has occurred; and controlling a resistance associated with the second phase of the repeated motion.

12. The method of claim 11, wherein the first phase comprises one of a concentric phase, the isometric hold phase, an eccentric phase, and the rest phase.

13. The method of claim 11, wherein the repeated motion is associated with an exercise that begins at a top position.

14. The method of claim 11, wherein the first phase comprises a concentric phase, wherein the second phase comprises the rest phase, and wherein the transition is detected at least in part by detecting a valid maximum.

15. The method of claim 11, wherein the first phase comprises the rest phase, wherein the second phase comprises an eccentric phase, and wherein the transition is detected at least in part by detecting that a position of the component of the exercise machine has decreased by at least a third threshold amount.

16. The method of claim 11, wherein the first phase comprises an eccentric phase, the second phase comprises the isometric hold state, and wherein the transition is detected at least in part by detecting a valid minimum.

17. The method of claim 11, wherein the repeated motion is associated with an exercise that begins at a bottom position.

18. The method of claim 17, wherein the first phase comprises a concentric phase, wherein the second phase comprises the isometric hold phase, and wherein the transition is detected at least in part by detecting a valid maximum.

19. The method of claim 17, wherein the first phase comprises the isometric hold phase, wherein the second phase comprises an eccentric phase, and wherein the transition is detected at least in part by detecting that a position of the component of the exercise machine has decreased by at least a fourth threshold amount.

20. The method of claim 17, wherein the first phase comprises an eccentric phase, wherein the second phase comprises the rest phase, and wherein the transition is detected at least in part by detecting a valid minimum.

21. The system of claim 1, wherein the detecting of the first phase of the repeated motion comprises to:

detect an extremum having an extremum parameter, wherein the extremum parameter includes a cable length detected extrema or a cable speed detected extrema; and match the extremum parameter with a previously determined signature associated with the user, wherein the previously determined signature relates to a predetermined repetition pattern.

\* \* \* \* \*